(12) United States Patent
Abt

(10) Patent No.: US 8,678,593 B2
(45) Date of Patent: Mar. 25, 2014

(54) OPHTHALMOSCOPIC CONTACT LENS

(75) Inventor: Niels A. Abt, Winterthur (CH)

(73) Assignee: Alcon Research, Ltd., Fort Worth, TX (US)

( * ) Notice: Subject to any disclaimer, the term of this patent is extended or adjusted under 35 U.S.C. 154(b) by 82 days.

(21) Appl. No.: 13/279,412

(22) Filed: Oct. 24, 2011

(65) Prior Publication Data

US 2012/0099077 A1    Apr. 26, 2012

Related U.S. Application Data

(60) Provisional application No. 61/406,846, filed on Oct. 26, 2010.

(51) Int. Cl.
*A61B 3/00*    (2006.01)
*A61B 3/10*    (2006.01)

(52) U.S. Cl.
USPC .......................................... 351/219; 351/212

(58) Field of Classification Search
USPC ................................................ 351/200–246
See application file for complete search history.

(56) References Cited

U.S. PATENT DOCUMENTS

| | | | |
|---|---|---|---|
| 1,605,725 | A | 11/1926 | Frederick |
| 1,782,331 | A | 11/1930 | Wilhelm |
| 2,129,305 | A | 9/1938 | Feinbloom |
| 2,177,933 | A | 10/1939 | Boeye |
| 2,247,628 | A | 7/1941 | Beitel, Jr. |
| 2,393,266 | A | 1/1946 | Riddell |
| 2,641,161 | A | 6/1953 | Silverstein |
| 3,001,441 | A | 9/1961 | Frederick |
| 3,102,157 | A | 8/1963 | Gamber |
| 3,212,097 | A | 10/1965 | Adler |
| 3,246,941 | A | 4/1966 | Moss |
| 3,290,927 | A | 12/1966 | Gambs et al. |
| 3,409,349 | A | 11/1968 | Boyle et al. |
| 3,431,046 | A | 3/1969 | Conrad et al. |
| 3,594,074 | A | 7/1971 | Rosen |

(Continued)

FOREIGN PATENT DOCUMENTS

| | | |
|---|---|---|
| CA | 2305892 C | 4/2006 |
| CH | 645263 A5 | 9/1984 |

(Continued)

OTHER PUBLICATIONS

International Searching Authority, International Search Report, PCT/US2011/057429, Mar. 9, 2012, 2 pages.

(Continued)

*Primary Examiner* — Mohammed Hasan

(57) ABSTRACT

An ophthalmoscopic surgical contact lens for placement on an eye of a patient is disclosed. The surgical contact lens includes an optic surrounded by a rim and at least one flange. The optic includes an aspheric anterior surface and a posterior surface having a shape substantially corresponding to the shape of a human cornea. The rim, comprising an edge surrounding the optic, provides the user with a gripping surface conducive to manual positioning and repositioning of the lens against a human eye. The flange may include a plurality of tabs extending from a periphery of the flange, wherein each tab is shaped and configured to conform to the curvature of a human sclera. Various embodiments of the contact lenses disclosed herein facilitate the visualization of structures within the interior of an eye, such as may be necessary during vitreoretinal surgical procedures.

20 Claims, 14 Drawing Sheets

(56) References Cited

U.S. PATENT DOCUMENTS

| | | |
|---|---|---|
| 3,630,602 A | 12/1971 | Herbert |
| 3,770,342 A | 11/1973 | Dudragne |
| 3,780,979 A | 12/1973 | Guillebon |
| 3,820,879 A | 6/1974 | Frisen |
| 3,884,238 A | 5/1975 | O'Malley |
| RE28,873 E | 6/1976 | Morgan |
| 4,056,310 A | 11/1977 | Shimizu |
| 4,126,904 A | 11/1978 | Shepard |
| 4,134,647 A | 1/1979 | Ramos-Caldera |
| 4,169,664 A | 10/1979 | Bailey, Jr. |
| 4,193,671 A | 3/1980 | Erickson et al. |
| 4,205,682 A | 6/1980 | Crock et al. |
| 4,212,226 A | 7/1980 | Teltscher |
| 4,265,519 A | 5/1981 | Pomerantzeff |
| 4,275,733 A | 6/1981 | Marinoff |
| 4,332,443 A | 6/1982 | Thomas |
| 4,378,147 A | 3/1983 | Fujita |
| 4,386,831 A | 6/1983 | Grounauer |
| 4,401,371 A | 8/1983 | Neefe |
| 4,410,245 A | 10/1983 | Koester |
| 4,452,514 A | 6/1984 | Spitznas |
| 4,469,413 A | 9/1984 | Shirayanagi |
| 4,470,159 A | 9/1984 | Peyman |
| 4,485,820 A | 12/1984 | Flower |
| 4,553,824 A | 11/1985 | Abe |
| 4,558,698 A | 12/1985 | O'Dell |
| 4,571,040 A | 2/1986 | Poler |
| 4,575,205 A | 3/1986 | Rappazzo |
| 4,581,379 A | 4/1986 | Nelson et al. |
| 4,605,524 A | 8/1986 | Danker |
| 4,618,229 A | 10/1986 | Jacobstein et al. |
| 4,646,720 A | 3/1987 | Peyman et al. |
| 4,721,378 A | 1/1988 | Volk |
| 4,728,183 A | 3/1988 | Heacock et al. |
| 4,801,198 A | 1/1989 | Heacock et al. |
| 4,810,082 A | 3/1989 | Abel, Jr. |
| 4,846,172 A | 7/1989 | Berlin |
| 4,897,079 A | 1/1990 | Zaleski et al. |
| 4,913,545 A | 4/1990 | Volk |
| 4,966,452 A | 10/1990 | Shields et al. |
| 4,990,150 A | 2/1991 | Tsubota et al. |
| 5,007,729 A | 4/1991 | Erickson et al. |
| 5,021,057 A | 6/1991 | Byrne, Jr. |
| 5,022,749 A | 6/1991 | Ogura |
| 5,041,098 A | 8/1991 | Loiterman et al. |
| 5,046,836 A | 9/1991 | Volk |
| 5,171,254 A | 12/1992 | Sher |
| 5,189,450 A | 2/1993 | Crossman et al. |
| 5,200,773 A | 4/1993 | Volk |
| 5,297,554 A | 3/1994 | Glynn et al. |
| 5,309,187 A | 5/1994 | Crossman et al. |
| 5,347,326 A | 9/1994 | Volk |
| 5,423,800 A | 6/1995 | Ren et al. |
| 5,436,680 A | 7/1995 | Volk |
| 5,523,810 A | 6/1996 | Volk |
| 5,589,896 A | 12/1996 | Mainster et al. |
| RE35,421 E | 1/1997 | Ruiz et al. |
| 5,623,323 A | 4/1997 | Johnson et al. |
| D382,399 S | 8/1997 | Hambleton et al. |
| 5,745,212 A | 4/1998 | Volk |
| 5,757,464 A | 5/1998 | Volk |
| 5,784,147 A | 7/1998 | Volk |
| 5,805,269 A | 9/1998 | Volk |
| 5,903,333 A | 5/1999 | Siminou et al. |
| 5,951,565 A | 9/1999 | Freeman |
| 5,953,097 A | 9/1999 | Stark |
| 5,963,301 A | 10/1999 | Volk |
| 6,034,827 A | 3/2000 | Nomura et al. |
| 6,092,898 A | 7/2000 | de Juan, Jr. |
| 6,120,147 A | 9/2000 | Vijfvinkel et al. |
| 6,164,779 A | 12/2000 | Volk |
| 6,412,946 B1 | 7/2002 | Vijfvinkel et al. |
| 6,641,589 B2 | 11/2003 | Kita |
| 6,698,886 B2 | 3/2004 | Pollack et al. |
| 6,767,098 B2 | 7/2004 | Erickson et al. |
| 6,976,758 B2 | 12/2005 | Khaw et al. |
| 7,021,760 B2 * | 4/2006 | Newman ................. 351/159.03 |
| 7,261,529 B2 | 8/2007 | Persyn et al. |
| 7,338,170 B2 | 3/2008 | Cech et al. |
| 7,419,262 B2 | 9/2008 | Whalen |
| 7,758,778 B2 | 7/2010 | Persyn et al. |
| 7,766,480 B1 | 8/2010 | Graham et al. |
| 7,766,904 B2 | 8/2010 | McGowan, Sr. et al. |
| 7,794,498 B2 * | 9/2010 | Pinchuk ...................... 623/6.56 |
| 7,946,706 B2 | 5/2011 | Cech et al. |
| 2003/0103191 A1 | 6/2003 | Staurenghi et al. |
| 2003/0109885 A1 | 6/2003 | Tano |
| 2005/0288697 A1 | 12/2005 | Tei et al. |
| 2007/0053990 A1 | 3/2007 | Persyn et al. |
| 2008/0107713 A1 | 5/2008 | Orilla et al. |
| 2008/0161845 A1 | 7/2008 | Murakami et al. |
| 2009/0312836 A1 * | 12/2009 | Pinchuk et al. .............. 623/6.37 |
| 2010/0036488 A1 | 2/2010 | De Juan, Jr. et al. |
| 2011/0090460 A1 | 4/2011 | Graham et al. |

FOREIGN PATENT DOCUMENTS

| | | |
|---|---|---|
| EP | 0042679 A2 | 12/1981 |
| EP | 0249329 B1 | 2/1991 |
| EP | 0442156 A1 | 8/1991 |
| EP | 0445994 A2 | 9/1991 |
| EP | 0445994 A3 | 4/1992 |
| EP | 1295579 A1 | 3/2003 |
| GB | 495191 A | 11/1938 |
| GB | 809894 A | 3/1959 |
| GB | 1084829 A | 9/1967 |
| GB | 1106229 A | 3/1968 |
| GB | 1360088 A | 7/1974 |
| GB | 1417650 A | 12/1975 |
| GB | 2016736 A | 9/1979 |
| GB | 2242835 A | 10/1991 |
| JP | 61109517 | 7/1986 |
| JP | 02-217818 | 8/1990 |
| JP | 02-224636 A | 9/1990 |
| JP | 02-241449 | 9/1990 |
| JP | 06-338184 | 12/1994 |
| JP | 2003024366 A | 1/2003 |
| JP | 2007007332 | 1/2007 |
| JP | 2007151739 A | 6/2007 |
| WO | 9314702 A1 | 8/1993 |
| WO | 9920171 A1 | 4/1999 |
| WO | 0055679 A1 | 9/2000 |
| WO | 2007030545 A2 | 3/2007 |
| WO | 2012058138 A1 | 5/2012 |

OTHER PUBLICATIONS

International Searching Authority, Written Opinion of the International Searching Authority, PCT/US2011/057429, Mar. 9, 2012, 6 pages.

Bausch & Lomb, Vitreoretinal Equipment Product Catalog, 2006, 28 pages. Mar. 2012.

Bovey, Etienne H., et al., A New Device for Noncontact Wide-Angle Viewing of the Fundus During Vitrectomy, Arch Ophthalmol., 1995, pp. 1572-1573, vol. 113. Dec. 1995.

Chalam, Kakarla V., et al., Newly Designed Self-retaining Contact Lens for Vitreous Surgery, America! Journal of Ophthalmology, 2003, pp. 544-546, vol. 135, Elsevier Science, Inc. Apr. 2003.

Chalam, Kakarla V., et al., Self retaining contact lens system for vitreous surgery, Indian J. Ophthalmol., 2004, pp. 67-71, vol. 52. Mar. 2004.

Chalam, K.V., et al., Two-Piece, Dual-Purpose Comprehensive Contact Lens for Vitreous Surgery, Ophthalmic Research, 2005, pp. 175-178, vol. 37. Jun. 21, 2005.

Chalam, Kakarla V., et al., Reusable Sutureless Silicone Ring for Housing Contact Lens During Vitreo-Retinal Surgery, Ophthalmic Communications Society, Inc., 2008, pp. 1550-1551. Jan. 1, 2008.

Chalam, Kakarla V., et al., Direct Image-Creating Aspheric Lens for Indirect Ophthalmoscopy, Ophthalmic Research, 2008, pp. 94-97, vol. 40. Jan. 25, 2008.

Chalam, Kakarla V., et al., Optics of Wide-Angle Panoramic Viewing System-Assisted Vitreous Surgery, Survey of Ophthalmology, 2004, pp. 437-445, vol. 49, No. 4, Elsevier. July.

(56) References Cited

OTHER PUBLICATIONS

Chong, Lawrence P., A Self-stabilizing Lens Ring for 25-Gauge Vitrectomy Surgery, American Journal of Ophthalmology, 2007, pp. 350-351, vol. 143, No. 2. Oct. 25, 2007.
Eckardt, B., et al., A New Convex-concave Contact Lens for Wide-angle Vitreoretinal Surgery with the BIOM, Lin. Mbl. Augenheilk, 1991, pp. 64-65, vol. 198. Jan. 1.
Alcon/Grieshaber, The Sew-On Contact Lens Set Catalog, 2005, p. 616., Jul. 21.
Alcon/Grieshaber, The Sew-On Contact Lens Set Catalog, 2006, p. 617., July.
Alcon/Grieshaber, The Grieshaber Infusion Contact Lens Set Catalog, 2005, p. 618., January.
Ikuno, Yasushi, et al., Sutureless Contact Lens Ring System During Vitrectomy, Am. J. Ophthalmol, 2002, pp. 847-848, vol. 133, Elsevier Science Inc., Jun. 2002.
De Juan, Eugene, et al., An Improved Contact-Lens Holder for Vitreous Surgery, Letters to the Journal, 1985, p. 213, vol. 99., No. 2., Oct.
Toth, Maj Cynthia a., et al, Letters to the Editor, New Instruments, Retina, 1993, pp. 353-355, vol. 13, No. 4., May 13.
Landers, et al., The optics of vitreous surgery, Am. J. Ophthalmol., 1981, abstract, vol. 91(5):611-4., Oct. 1.
Landers, Maurice B., III., et al., A New, Non-contact Wide Field Viewing System for Vitreous Surgery, Am. J. Ophthalmol, 2003, pp. 199-201, vol. 136, No. 1, Elsevier Inc., Jul., 2003.
Lewis, John Michael, et al., A Technique for Contact Lens Fixation During Vitreous Surgery, Ophthalmic Surgery and Lasers, 1996, pp. 891-893, vol. 27, No. 10., Dec.
Nakata, Ko, et al., Wide-angle Viewing Lens for Vitrectomy, American Journal of Ophthalmology, 2004, pp. 760-762, vol. 137, Elsevier, Inc., Jul.
http://www.optikon.com/en/download-depliant.asp; archive dated Mar. 23, 2009, 9 pages.
Rufer, Florian, et al., White-to-White Corneal Diameter, Cornea, Clinical Sciences, 2005, pp. 259-261, vol. 24, No. 3., Feb.
Shah, Vinay A., et al., Self-Stabilizing Wide-Angle Contact Lens for Vitreous Surgery, Retinal, The Journal of Retinal and Vitreous Diseases, 2003, pp. 667-669, vol. 23, No. 5., May.
Shah, Vinay A., et al., Suction-Assisted One-Piece Self-Retaining Wide-Angle Contact Lens for Vitrectomy, Ophthalmic Research, 2003, pp. 170-172, vol. 35. Jun.
Shah, Vinay A., et al., Newly Designed Self-Retaining Prism Contact Lens for Vitreous Surgery, Retina, The Journal of Retinal and Vitreous Diseases, 2003, pp. 721-722, vol. 23, No. 5., Jan.
Synergetics, Inc., Synergetics Vitreretinal Catalog, 2009, p. 33., Jul.-Aug. 2009.
Shields, M. Bruce, et al., A Contact Lens for Transscleral Nd:YAG Cyclophotocoagulation, American Journal of Ophthalmology, 1989, pp. 457-458, vol. 108, No. 4, June.
De Souza, Osias Francisco, et al., Pars plana vitrectomy with the "reinverting operating lens system:" a step-up in vitreo retinal surgery, Arq. Bras. Oftalmol., 2003, pp. 315-319, vol. 66. May/Jun. 2003.
Spitznas, Manfred, A binocular indirect ophthalmomicroscope (BIOM) for non-contact wide-angle vitreous surgery, Graefe's Archive for Clinical and Experimental Ophthalmology, 1987, pp. 13-15, vol. 225. Jun.
Stefansson, Einar, et al., Refractive Changes from Use of Silicone Oil in Vitreous Surgery, Retina, 1988, abstract, vol. 8(1). Dec. 6.
Tei, Mamoru, et al., A New Non-Trocar System for 25-guage Transconjunctival Pars Plana Vitrectomy, American Journal of Ophthalmology, 2005, pp. 1130-1133, vol. 139, No. 6. Nov. 13.
Vignal, R., et al., [Improved visualization of fundus with green-light ophthalmoscopy], J. Fr. Ophtalmol., 2007, abstract, vol. 30(3). Nov. 3.
Volk Optical, Inc., [ ophthalmic catalog ], 2006, 32 pages. Mar. 13.
Zhao, Huawei, et al., The effect of chromatic dispersion on pseudophakic optical performance, British Journal of Ophthalmology, 2007, 8 pages. May 2, 2007.
Ocular Instruments Catalog archive—Portion of http://www.ocular-instruments.com/html/catalog/index.asp? sect=surglenses (Internet archive dated Mar. 11, 2006).
Ho, Patrick C., et al., Fundus Contact Lenses for Closed Pars Plana Vitrectomy, Ophthalmology • Insrument and Book Supplement, 1983, pp. 106-114. no date.
Casparis, Heather, et al., Sutureless Lens Ring Fixation for Vitrectomy Using Cellulose Eye Drain, Surgical Technique, 2010, pp. 1544-1545. Oct. 30.
Parel, Jean-Marie, et al., Steam-Sterilizable Fundus Contact Lenses, Arch Ophthalmol, 1981, p. 151, vol. 99. Jan. 1.
Huamonte, Felipe U., et al., Lens Holder and Modified Contact Lens for Pars Plana Vitrectomy, Arch Ophthalmol, 1981, p. 154, vol. 99. Jan. 1.
Kadonosono, Kazuaki, et al., Multicoated Contact Lens for Bimanual Vitreous Surgery Without Endoillumination, Arch Ophthalmol, 2004, pp. 367-368, vol. 122. Mar. 1.

* cited by examiner

OPHTHALMOSCOPIC CONTACT LENS

CROSS-REFERENCE TO RELATED APPLICATIONS

This application claims the benefit of priority of U.S. Provisional Patent Application Ser. No. 61/406,846 titled "Ophthalmoscopic Contact Lens", filed on Oct. 26, 2010, whose inventor is Niels A. Abt, which is hereby incorporated by reference in its entirety as though fully and completely set forth herein.

BACKGROUND

The present disclosure relates to a self-retaining contact lens for observation and surgical treatment of the vitreous or retina of the eye, and more particularly for use in vitreoretinal surgery.

Anatomically, the eye is divided into two distinct parts—the anterior segment and the posterior segment. The anterior segment includes the lens and extends from the outermost layer of the cornea (the corneal epithelium) to the posterior of the lens capsule. The posterior segment, which is much larger than the anterior segment, includes the portion of the eye behind the lens capsule. The posterior segment extends from the anterior hyaloids face to the retina, with which the posterior hyaloid face of the vitreous body is in direct contact, and further to the choroid and the posterior sclera.

The posterior segment includes the vitreous body, which is a clear, colorless, gel-like substance. The vitreous body gives the eye its globular shape and form, and comprises approximately two-thirds of the total volume of the eye. It is composed of 99% water and 1% collagen and sodium hyaluronate. The anterior boundary of the vitreous body is the anterior hyaloid face, which touches the posterior capsule of the lens, and the posterior boundary of the vitreous body is the posterior hyaloid face, which is in contact with the retina. The vitreous body, unlike the aqueous humor in the anterior chamber, is not free-flowing and has normal anatomic attachment sites. These sites include the optic nerve head, the macula lutea, the vascular arcade, and the vitreous base, which is a 3-4 mm wide band that overlies the ora serrata. The vitreous body's major functions are to hold the retina in place, maintain the integrity and shape of the globe, absorb shock due to movement, and to give support for the posterior aspect of the lens.

In contrast to aqueous humor, the vitreous body is not continuously replaced, and it becomes more fluid with age through a process known as syneresis. Syneresis results in shrinkage of the vitreous body, which can exert pressure or traction on its normal attachment sites. If enough traction is applied, the vitreous body may pull itself from its retinal attachment and create a retinal tear or hole, which may necessitate surgical repair.

Vitreoretinal surgical procedures are used to treat many serious conditions of the posterior segment, including age-related macular degeneration (AMD), diabetic retinopathy, and diabetic vitreous hemorrhage, macular holes, retinal detachment, epiretinal membrane, cytomegalovirus (CMV) retinitis, and many other ophthalmic conditions. When performing surgery of the posterior segment of the eye, as in vitreoretinal surgery, it is typically necessary to view the anatomy of the eye with an operating microscope and an ophthalmoscopy lens designed to provide a clear image of the posterior segment. Generally, a standard operating microscope is able to view the structures of the anterior segment of the eye and the anterior portion of the posterior segment of the eye, but cannot adequately view the entire posterior segment of the eye because the natural optics of the eye (i.e., the cornea and the lens) prevent the operating microscope from focusing on some structures in the posterior segment of the eye (e.g., the retina). Therefore, in order to focus the operating microscope on structures such as the retina, an ophthalmoscopy lens with appropriate optical properties may be positioned between the eye and the microscope to compensate for the natural optics of the eye.

The surgeon may make several tiny incisions (e.g., approximately one millimeter in length) in the sclera at the pars plana. The surgeon inserts microsurgical instruments through the incisions, such as a fiberoptic light source to illuminate inside the eye, an infusion line to maintain the eye's shape during surgery, and various instruments to cut and remove the vitreous body (e.g., a vitrectomy probe) or to manipulate tissue such as membranes or the retina itself.

Direct ophthalmoscopy lenses which create a virtual image within the eye and indirect ophthalmoscopy lenses which create a real image outside of the eye are two lens types which have been used for observation of the posterior segment and as aids in the surgical treatment of the eye. Known lenses that are used in vitreoretinal surgery may suffer from less than desirable image quality due to loss of contrast and sharpness secondary to various optical phenomena, such as, by way of non-limiting example, defocusing, spherical aberration, coma, distortion, and chromatic aberration.

The devices and systems disclosed herein overcome one or more of the deficiencies of the prior art.

SUMMARY

The disclosure relates generally to, and encompasses, an apparatus and system for visualizing the interior of an eye, and more specifically to a ophthalmoscopic contact lens for use during an ophthalmoscopic surgery or procedure involving visualization of the posterior segment.

In one exemplary embodiment, an ophthalmoscopic contact lens comprises an optic, a flange, and a rim. The optic may include an anterior surface having an aspheric base profile and a posterior surface having a shape substantially corresponding to a shape of a cornea of an eye. The flange may be integrally formed with the optic and surround the optic, and have a curvature substantially corresponding to the curvature of a sclera of an eye. The rim may surround the optic and may extend from an anterior surface of the flange to and beyond the anterior surface of the optic.

In another exemplary embodiment, an ophthalmoscopic contact lens comprises an optic, a flange, and a plurality of tabs. The optic may include an anterior surface having an aspheric base profile and a posterior surface having a shape substantially corresponding to a shape of a cornea of an eye. The flange may be integrally formed with the optic and surround the optic, and have a curvature substantially corresponding to the curvature of a sclera of the eye. The plurality of tabs may extend from the flange and have a curvature adapted to fit a sclera of the eye.

In another exemplary embodiment, an ophthalmological surgical system comprises a surgical contact lens and a packaging case. The surgical contact lens may comprise an optic and a flange. The optic may include an anterior surface having an aspheric base profile and a posterior surface having a shape substantially corresponding to a shape of a cornea of an eye. The flange may be integrally formed with the optic and surround the optic. The packaging case may comprise a top portion and a bottom portion, wherein the top portion and the bottom portion are shaped and configured to close together and contain the lens.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

Figure 1:
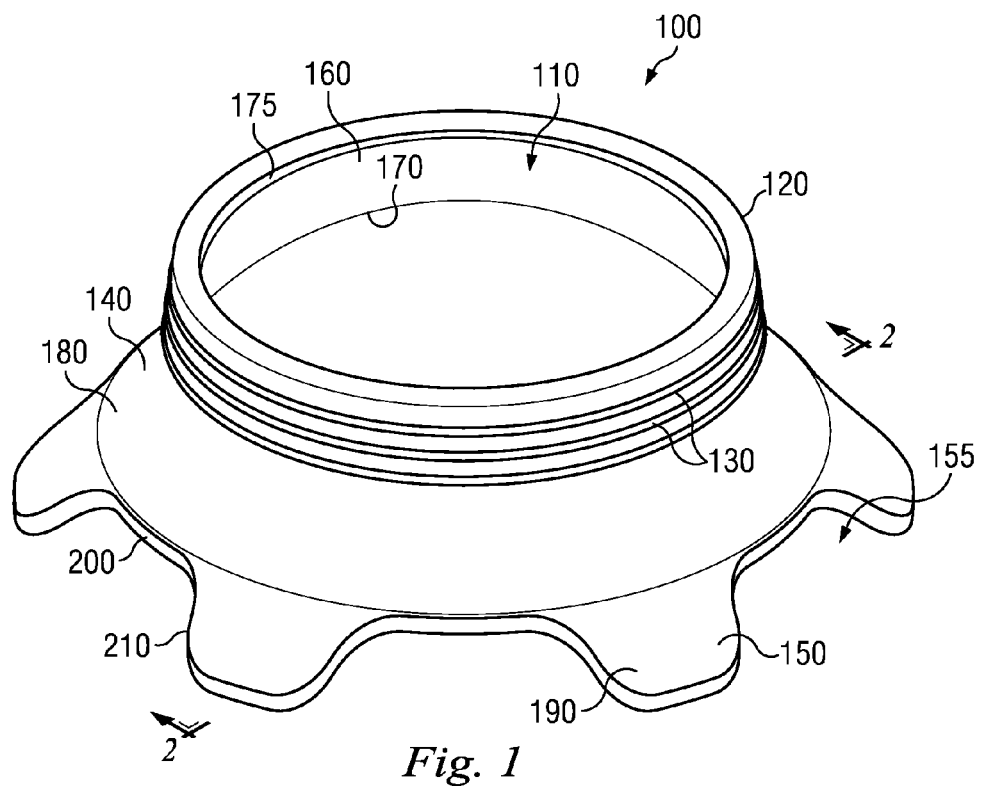
FIG. 1 illustrates a perspective view of a contact lens according to one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates generally to ophthalmoscopic contact lenses used in ophthalmic surgeries, such as vitreoretinal surgeries or other posterior segment surgeries. In some instances, embodiments of the present disclosure may be configured to be part of an ophthalmic surgical system. The present disclosure provides a surgical contact lens utilizing an aspheric optic to better visualize the interior of the eye, including the posterior segment, by providing enhanced contrast and sharper visualization throughout the field of view. Moreover, the surgical contact lenses of the present disclosure include a concave inner surface that mimics the curvature of the cornea and at least one flange that extends from or supports the lens against the cornea and/or sclera, allowing the contact lens to be self-stabilized and self-retained on the eye throughout the surgery (i.e., without the use of sutures or a manually held handle). Therefore, the ophthalmoscopic contact lenses disclosed herein may enhance stabilization of the lens and utilize aspheric optics (i.e., optical lenses) to provide better visualization of the interior of the eye than conventional lenses, thereby facilitating hands-free operation and the diagnosis and the treatment of various eye conditions.

FIG. 1 illustrates an ophthalmoscopic contact lens 100 according to one embodiment of the present disclosure. Though the contact lens 100 shown in FIG. 1 is configured for use in ophthalmologic surgeries, such as vitreoretinal surgery, the contact lens may be used in any ophthalmological context, including diagnosis, treatment, ex vivo evaluation, and post-mortem evaluation. The contact lens 100, which is capable of self-retaining placement on the eye of a patient throughout a surgical procedure, enhances visualization of structures within the interior of an eye, such as within the posterior segment during a vitreoretinal procedure. The contact lens 100 may comprise a direct ophthalmoscopy lens, for example, of the plano-concave, convex-concave (meniscus), or bi-concave type, or alternatively may be part of a multi-element indirect ophthalmoscopy lens. The contact lens 100 may also be capable of stabilizing surgical instruments and providing irrigation during an ophthalmological procedure. Some embodiments of the contact lens 100 may be configured as disposable single-use lenses, thereby facilitating optimum optics through a new contact lens for each patient.

The surgical contact lens embodiments disclosed herein may be used in combination with a surgical microscope to view the interior of an eye. Such a surgical microscope may be spaced from and cooperate with an embodiment of the surgical contact lens of the present disclosure for capturing light rays exiting the eye through the cornea and passing through the contact lens. The surgical microscope can focus such light rays to create an image of, for example, the retina and the vitreous body.

In the pictured embodiment, the contact lens 100 comprises a one-piece device including integrally formed components. The lens 100 includes a central lens portion or optic 110 circumferentially surrounded by and integrally formed with a cylindrical rim 120, which includes gripping features 130. A circular flange 140, which is integrally formed with the rim 120, extends from and angles away from the rim 120, and a plurality of tabs 150 project outward from the flange 140. A recess 155 is located between any two tabs 150.

The optic 110 is shaped and configured for viewing interior regions of the eye. In some embodiments, the optic 110 may be sized to have an active diameter of approximately 10 mm, which is larger than a typical dilated pupil, to provide adequate light through the optic 110 while remaining small enough to limit interference with a surgeon's hand during an ophthalmological procedure.

Figure 2:
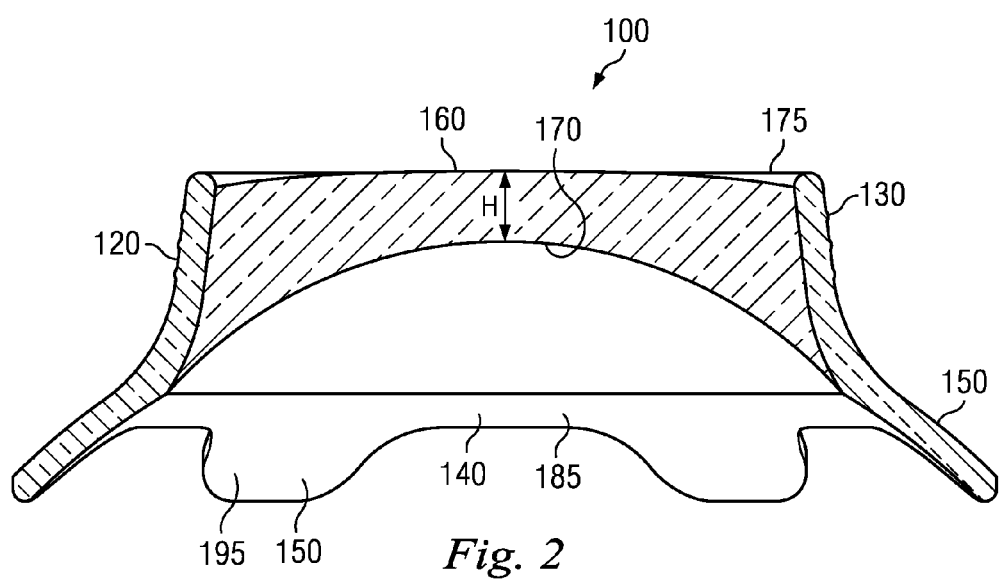
FIG. 2 illustrates a partially cross-sectional side view of the contact lens shown in FIG. 1 according to one embodiment of the present disclosure.

As shown in FIGS. 1 and 2, the optic 110 includes an aspheric anterior optic surface or base profile 160 and a posterior optic surface 170 having a curved spherical shape substantially corresponding to the shape of an average human cornea. The aspheric shape of the anterior optic surface 160 allows for enhanced visualization throughout the field of view in comparison to traditional lens geometry by better compensating for, by way of non-limiting example, off-axis stereo viewing, defocus, loss of contrast, and loss of peripheral sharpness.

The aspheric anterior optic surface 160 is desirable to eliminate spherical aberrations of the eye when visualizing the interior of the eye and to adjust the plane of focus to the curvature of, for example, the retina, which is a light-sensitive, curved layer of tissue lining the inner surface of the eye. When the curved surface of the retina is viewed through a surgical microscope without compensation, only a band of sharp focus will exist. Therefore, the user must adjust the microscope to view structures outside of the sharply focused band and then shift back in the original band. The aspheric curvature of the anterior optic surface 160 adjusts the plane of focus to the curvature of the retina so that all of the structures within a circular region of interest are in focus while also correcting for spherical aberrations of the ocular components (such as, by way of non-limiting example, the cornea and the lens).

After determining the desired lens properties, the aspheric shape of the optic 110 may be optimized by considering both the varied curvature of the retina and the off-axis alignment of the microscope. Optimization of the optics 110 will improve image sharpness and image contrast (especially at the periphery) while maintaining image sharpness and contrast in the optical axis.

In some embodiments, the anterior optic surface 160 includes an anti-reflective or non-reflective coating to reduce reflective glare for improved visualization. A non-reflective or anti-reflective coating may improve the ability to capture video for recording purposes by reducing or eliminating artifacts in a 2-dimensional microscope view.

Figure 4:
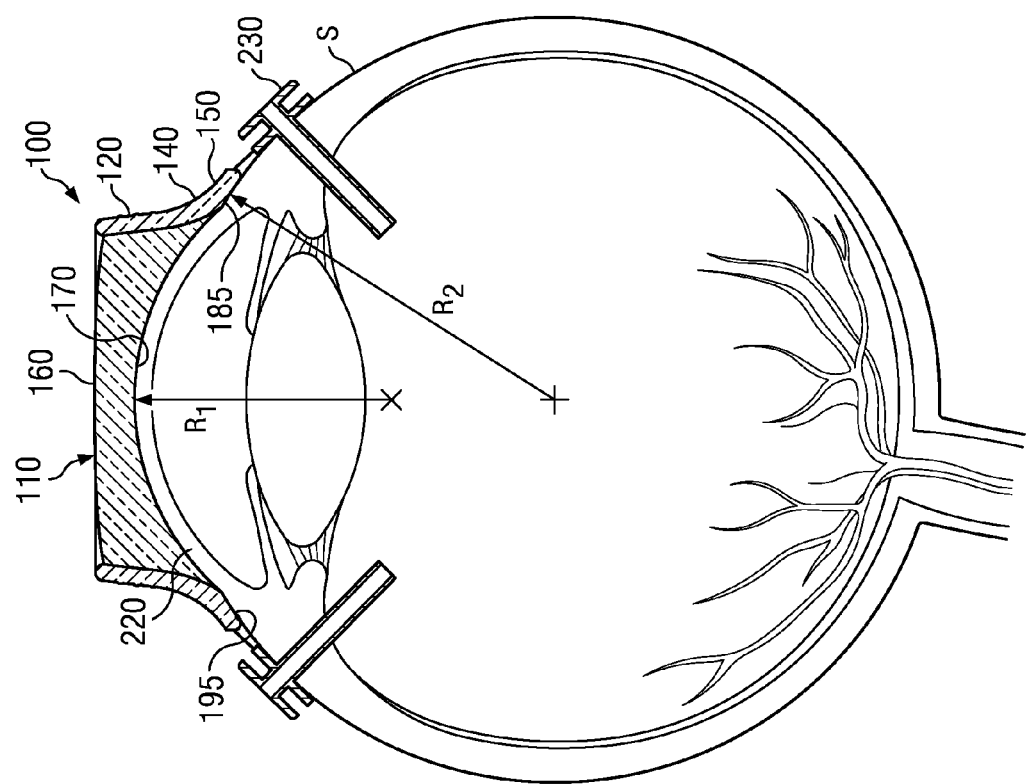
FIG. 4 illustrates a cross-sectional side view of the contact lens shown in FIG. 1 according to one embodiment of the present disclosure, positioned on an eye.

As shown in FIG. 4, the posterior optic surface 170 comprises an interior concave surface that is configured to have a radius of curvature $R_1$ for contacting to cornea. As such, in some embodiments, the posterior optic surface 170 may have an apical radius $R_1$ of approximately 7.0 to 8.5 mm, and preferably may be approximately 7.8 mm.

The various embodiments of the surgical contact lens of the present disclosure may include optics having different diopter powers. The diopter power of a lens is reflection of the optical power of the lens, which is equal to the reciprocal of the focal length of the lens as measured in meters. A typical cornea, for example, has an optical power of 42 diopters, and a typical human lens has an optical power of 18-30 diopters. As a result, a typical unaccommodated eye may have an optical power of 65 diopters. The diopter power of the surgical contact lens may be chosen to obtain a desired balance between the field of view and the magnification. A surgical contact lens having an optical power of −65 diopters would cancel out the cornea's effect, thereby providing a large field of view, but without magnification. A surgical contact lens having an optical power of more or less than −65 diopters will provide either an increased field of view with less magnification or a reduced field of view with higher magnification. For example, a surgical contact lens having an optical power of −59 diopters would be close to cancelling out the corneal power while providing a greater field of view (i.e., approximately a 30 degree field of view) and less magnification than a lens having an optical power of −41 diopters. Various embodiments of the surgical contact lenses described herein may implement both the aforementioned optical powers.

With reference to FIGS. 1 and 2, the rim 120 comprises a ridge or rim extending around a peripheral circumference of the optic 110 that provides the user with a gripping surface for the surgical contact lens 100. The rim 120 comprises a cylindrical tube that circumferentially surrounds the optic 110, supplying a gripping surface (other than the optic itself) for the user and providing a protective edge 175 that surrounds the periphery of the anterior optic surface 160. The rim 120 allows the user (e.g., the surgeon or other operating room personnel) an area on the contact lens to use for repositioning or otherwise moving the lens without having to touch and possibly affect the optic 110. The rim 120, by providing a separate contact surface, may also function to protect the optic 110 from damage while the surgical contact lens 100 is securely contained within packaging. An exemplary embodiment of the packaging is described in further detail below in reference to FIGS. 18a-18d.

In the pictured embodiment, the edge 175 of the rim 120 extends above the anterior optic surface 160. In other embodiments, the edge 175 may extend circumferentially around the optic 110 without extending above the anterior optic surface 160. In the pictured embodiment, the gripping features 130 encircle the rim 120 and allow the user to manipulate (i.e., by way of non-limiting example, grasp, grip, lift and/or push) the contact lens 100 and manually position and/or reposition the contact lens 100 when the lens 100 is lying against a surface (e.g., an eye). In particular, the user may grasp the gripping features 130 of the rim 120 to manually position or reposition the contact lens 100 without contacting or smudging the optic 110. In the pictured embodiment, the gripping features 130 comprise raised ridges spaced apart and in parallel with each other. In other embodiments, the gripping features may be shaped and configured as any of a variety of textured features, including, by way of non-limiting example, grooves, protrusions, and/or perforations. In some embodiments, the gripping features may be positioned on the rim without encircling the rim.

The circular flange 140 encircles and extends away from the rim 120 at an angle, forming a peripheral flared region surrounding a base circumference of the optic 110. As shown in FIGS. 1 and 2, the flange 140 forms an integral extension of the rim 120, and extends radially from the optic 110 such that if the surgical contact lens 100 is centrally positioned over a cornea of an eye, the flange 140 would extend onto the sclera of the eye. The flange 140 is shaped and configured to be thin enough to provide some pliancy. For example, the flange 140 may be pliant enough to allow for rotation on the eye if necessary. In alternate embodiments, the flange may be semi-rigid or rigid. The flange 140 may be shaped and configured to be transparent enough to provide for visualization through the flange to observe, by way of non-limiting example, underlying tissue, vessels, air bubbles, and/or bleeding. In alternate embodiments, the flange may be semi-transparent or opaque. In some embodiments, the flange may be thinner or wider than flange 140.

The flange 140 includes an anterior flange surface 180 and a posterior flange surface 185. The posterior flange surface 185 is shaped and configured to have a different curvature from that of the posterior optic surface 170. For example, in the pictured embodiment shown in FIG. 2, the posterior flange surface 185 has a curved shape substantially corresponding to the curvature of a sclera of an average human eye, thereby allowing the flange 140 to sit approximately flush against the sclera of the eye while the optic 110 sits approximately flush against the cornea of the eye. Thus, in various embodiments, the curvature of the posterior flange surface may be substantially flatter than the curvature of the posterior optic surface. This combination of varying curvatures conforming to different portions of an average human eye tends to center and stabilize the lens over the cornea of the eye.

The tabs 150 comprise extensions of the flange 140 that extend away from the rim 120 at an angle and are shaped to conform to the curvature of an average human sclera. In other words, the tabs 150 comprise extensions or feet extending from and forming the farthest periphery of the flange 140 from the optical axis of the eye. The tabs 150 may be shaped in any of a variety of shapes, including, by way of non-limiting example, triangles, oblongs, and finger-like extensions. In some embodiments, the tabs 150 are shaped and configured to be thin enough to provide some pliancy. For example, the tabs 150 may be pliant enough to allow for rotation on the eye if necessary. The tabs 150 may be shaped and configured to be transparent enough to provide for visualization through the tabs to observe, by way of non-limiting example, underlying tissue, vessels, air bubbles, and/or bleeding. In alternate embodiments, the tabs may be semi-transparent or opaque. In some embodiments, the tabs may be thinner or wider than the tabs 150.

As shown in FIGS. 1 and 2, each tab 150 includes an anterior tab surface 190 and a posterior tab surface 195. In the pictured embodiment, each posterior tab surface 195 has a curved shaped substantially corresponding to the curvature of the sclera of the eye, thereby allowing the tabs 150 to sit approximately flush against the eye.

As shown in FIG. 1, each recess 155 is shaped and defined by a periphery 200 of the flange 140 and a periphery 210 of the tabs 150. The number of recesses 155 corresponds to the number of tabs 150. For example, in the pictured embodiment, the lens 100 includes six tabs 150 and six recesses 155. Each recess 155 is capable of engaging with a surgical instrument such as, by way of non-limiting example, a trocar cannula positioned on the sclera of the eye.

In some embodiments, the lens 100 may include a low-profile optic 110 having a height H extending from the posterior optic surface 170 to the anterior optic surface 160, as shown in FIG. 2. For example, the low-profile optic 110 may have a height H of approximately 1.00 mm to 2.00 mm, and preferably may be approximately 1.22 mm. In other embodiments, the lens 100 may include a high-profile optic (and surrounding rim) where the height H of the optic is larger. For example, the high-profile optic may have a height H of approximately 1.50 mm to 2.00 mm, and preferably may be approximately 1.90 mm. However, it should be noted that in other embodiments the height H may be less than 1.00 mm or more than 2.00 mm, and that no limitation of height H is implied by the ranges provided herein.

Figure 3:
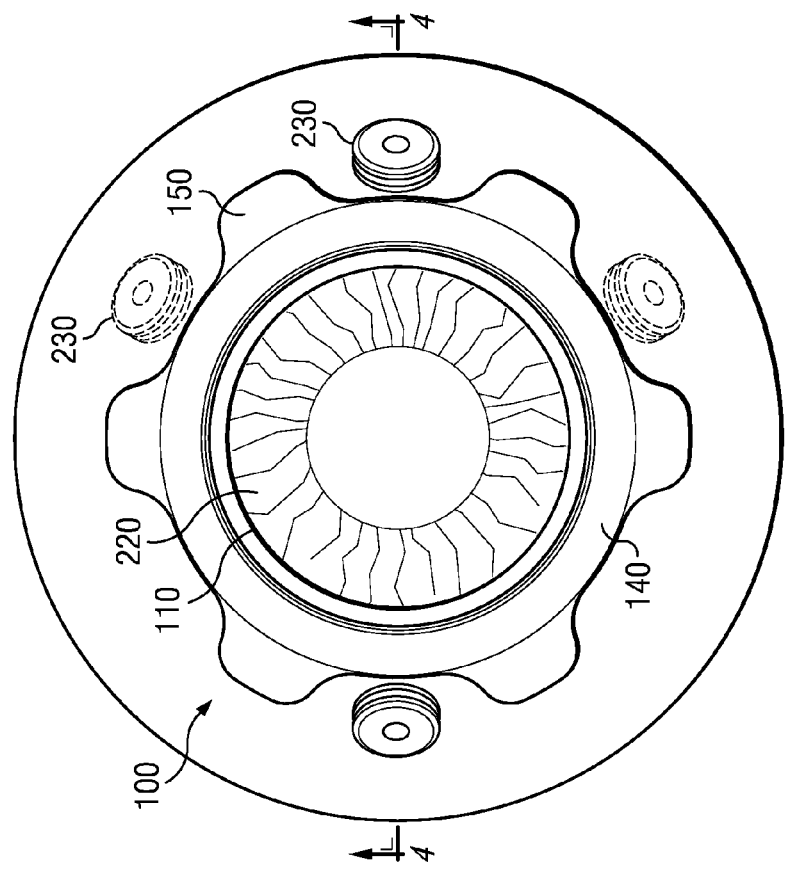
FIG. 3 illustrates a top plan view of the contact lens shown in FIG. 1 according to one embodiment of the present disclosure, in relation to a cornea.

FIG. 3 illustrates the surgical contact lens 100 according to one embodiment of the present disclosure positioned on an average human eye, with the optic 110 overlying the cornea 220 and the flange 140 and the tabs 150 resting upon the sclera. The tabs 150 may limit the free available space for the lens 100 to move due to the tabs 150 contacting and/or interacting with surgical instruments on the eye such as, by way of non-limiting example, trocar cannulas 230 positioned near the lens. In the pictured embodiment, the lens 100 includes six tabs 150. Having six tabs 150 allows for multiple placement options for the surgical contact lens 100. The recesses 155 are sized to be large enough to accommodate a trocar cannula while still providing space for movement to account for variations in placement of the cannulas and for adjustment of the lens position.

Although the contact lens 100 pictured in FIG. 3 includes six finger-like extensions or tabs 150, other embodiments may not include tabs or may include any number of tabs (e.g., more or less than six tabs). The number and curvature of the tabs 150 may be selected to conform around areas on an average human eye at which trocar cannulas are typically placed for a posterior segment ophthalmological surgical procedure (i.e., a surgical procedure involving the posterior segment or posterior chamber of the eye).

For example, a typical vitreoretinal surgery requires placement of three trocar cannulas to provide ports for entry of surgical instruments and fluid into the eye. Typically, one port is used for fluid infusion and two ports are used for instrument insertion (e.g., one active port and one illumination port). Trocar cannulas are typically positioned such that they are spaced 3.5-4.5 mm away from the limbus of the eye (where the pars plana is located), which has an average diameter of approximately 11.7 mm, to avoid damage to the ciliary processes and the ora serrata. Therefore, as shown in FIG. 3, the trocar cannulas 230 are preferably placed in a small annular band. Given that the trocar cannulas are typically placed on the eye in a generally triangular pattern, as shown in FIG. 3, the pictured embodiment includes six symmetrically-placed tabs 150 to facilitate easier lens placement among the three trocar cannulas 230. The trocar cannulas indicated in dashed lines correspond to desirable trocar cannula positions for surgery depending upon whether surgery is performed on the right eye or the left eye. Thus, one of the dashed line trocars would typically not be present during use of the lens on either the right eye or the left eye.

FIG. 4 illustrates a cross-sectional view of the surgical contact lens 100 positioned against an eye. As illustrated in FIG. 4, the contact lens 100 is configured to provide excellent self-retention against the eye, thereby allowing hands-free operation of the contact lens 100. The self-retaining aspects of the present disclosure are provided by at least one combination of various features. One such feature is the large surface area of the posterior optic surface 170, the flange 140, and the tabs 150. In the pictured embodiment, the posterior optic surface 170, the posterior flange surface 185, and the posterior tab surfaces 195 contact the anterior surface of the eye (i.e., the cornea and/or the sclera S) to enable the lens 100 to be self-retaining on the eye through capillary traction. As a result, separate means for holding the lens against the eye are not required. In some embodiments, the lens 100 includes more than 200 square millimeters of surface contact area.

As shown in FIG. 4, the posterior flange surface 185 and the posterior tab surfaces 195 comprise interior concave surfaces that are configured to have a radius of curvature $R_2$ for contacting the sclera S. As such, in some embodiments, the posterior flange surface 185 and the posterior tab surfaces 195 may have apical radii $R_2$ of approximately 11.0 to 12.0 mm. In particular, the posterior optic surface 170 may be congruent to the surface of the cornea while the posterior flange surface 185 and the posterior tab surfaces 195 may be congruent to the surface of the sclera S, providing a form factor adapted to hold the lens in position on the eye. The self-retaining nature of the contact lens 100, provided by the shapes and contours of the posterior optic surface 170, the posterior flange surface 185, and the posterior tab surfaces 195, eliminate the need for suturing or holding of the lens 100 during use that is often required by prior art ophthalmoscopic contact lenses.

Further, the surgical contact lens 100 may be fitted on the cornea with the use of an interface solution, such as, by way of non-limiting example, a viscoelastic or other agent. The use of an interface agent between the lens 100 and the cornea 220 will provide for high shear forces between the lens and the cornea, increasing the self-retention capabilities of the lens. Specifically, the posterior optic surface 170, the posterior flange surface 185, and/or the posterior tab surfaces 195 may generate sufficient shear forces with the interface solution placed between the lens 100 and the cornea 220 (and the sclera S) to self-retain the lens 100 during use. In addition to increasing the shear forces between the ocular tissue and the lens 100, the interface solution functions to keep the cornea hydrated and prevent the cornea from drying out during use of the lens 100.

The various contact lens embodiments described herein can stabilize and self-retain their position on an eye and move with the eye as necessary during a surgical or diagnostic procedure. Although the various contact lens embodiments described herein may be used without the aid of an assistant's handle, in some embodiments, the contact lens embodiments may be used in conjunction with a handle to provide increased control and/or maneuverability of the contact lens on the eye.

Figure 5:
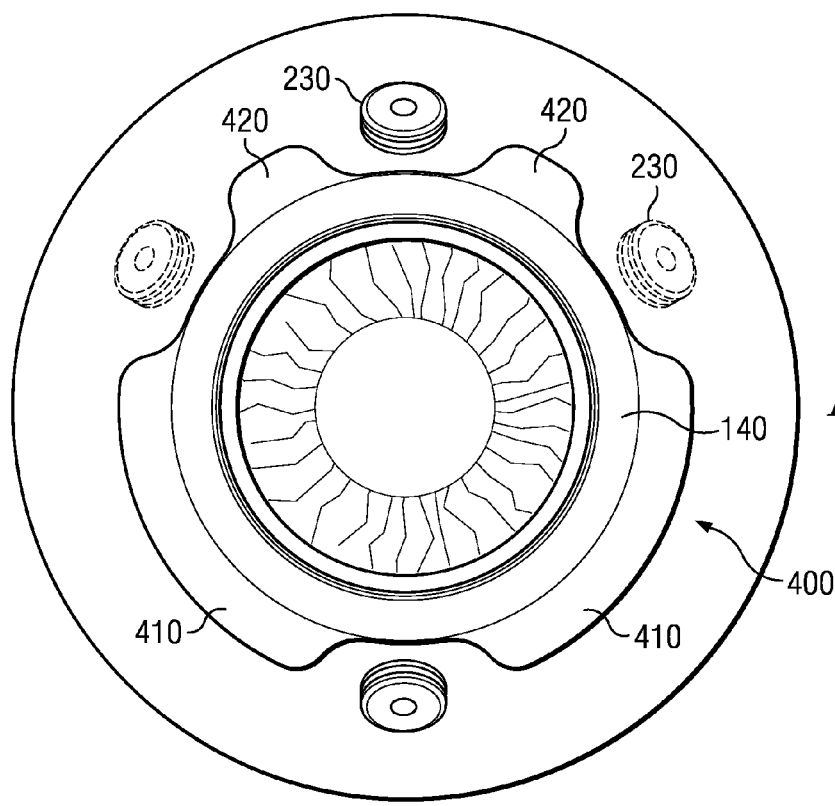
FIG. 5 illustrates a top plan view of a contact lens according to one embodiment of the present disclosure, in relation to a cornea.

FIG. 5 illustrates a surgical contact lens 400 according to one embodiment of the present disclosure. The surgical contact lens 400 is similar to the surgical contact lens 100 except for the differences noted herein. The lens 400 includes two tabs 410 and two tabs 420 extending from flange 140, thereby providing increased surface contact area between the lens 400 and an eye. The tabs 410 are wider than the tabs 420. In some embodiments, the lens 400 may include a wider flange than the flange 140 shown in FIG. 5. Various embodiments may include any number and arrangement of tabs 410, 420 that permit the appropriate insertion of at least three trocar cannulas 230.

Figure 6:
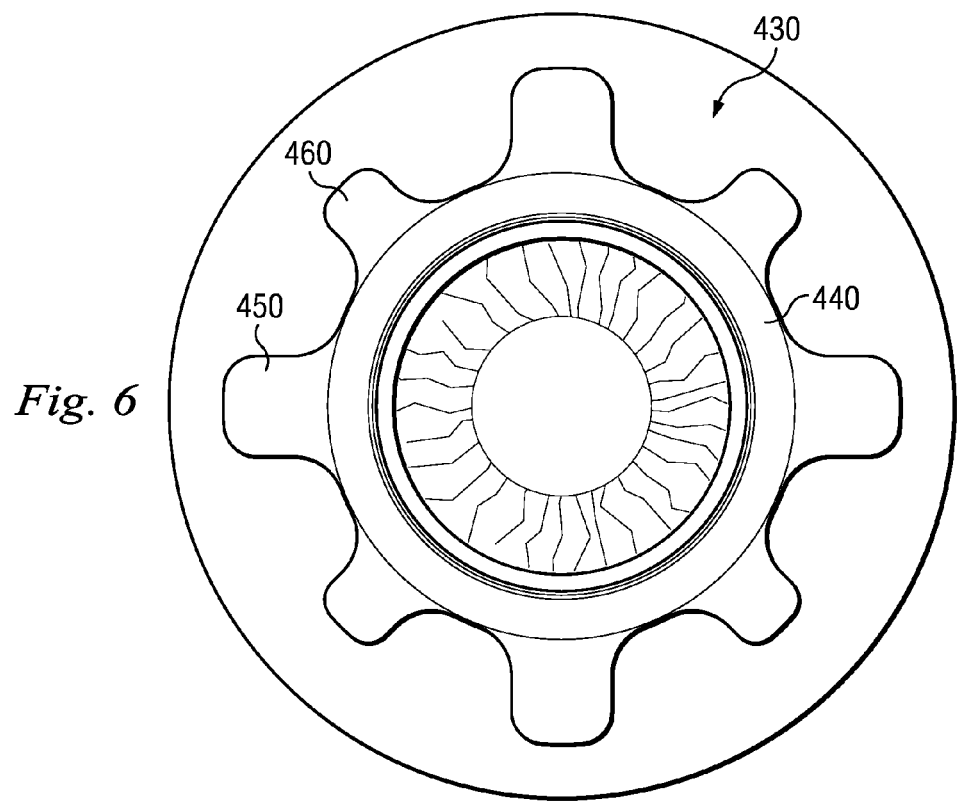
FIG. 6 illustrates a top plan view of a contact lens according to one embodiment of the present disclosure, in relation to a cornea.

FIG. 6 illustrates a surgical contact lens 430 according to one embodiment of the present disclosure. The surgical contact lens 430 is similar to the surgical contact lens 100 except for the differences noted herein. The lens 430 includes a flange 440, tabs 450, and tabs 460. The tabs 450, 460 may be shaped as finger-like extensions of different lengths. In the pictured embodiment, the tabs 450 are longer than the tabs 460, and extend further from the flange 440 than the tabs 460. Various embodiments may include any number and arrangement of tabs 450, 460 that permit the appropriate insertion of the trocar cannulas 230.

Figure 7A:
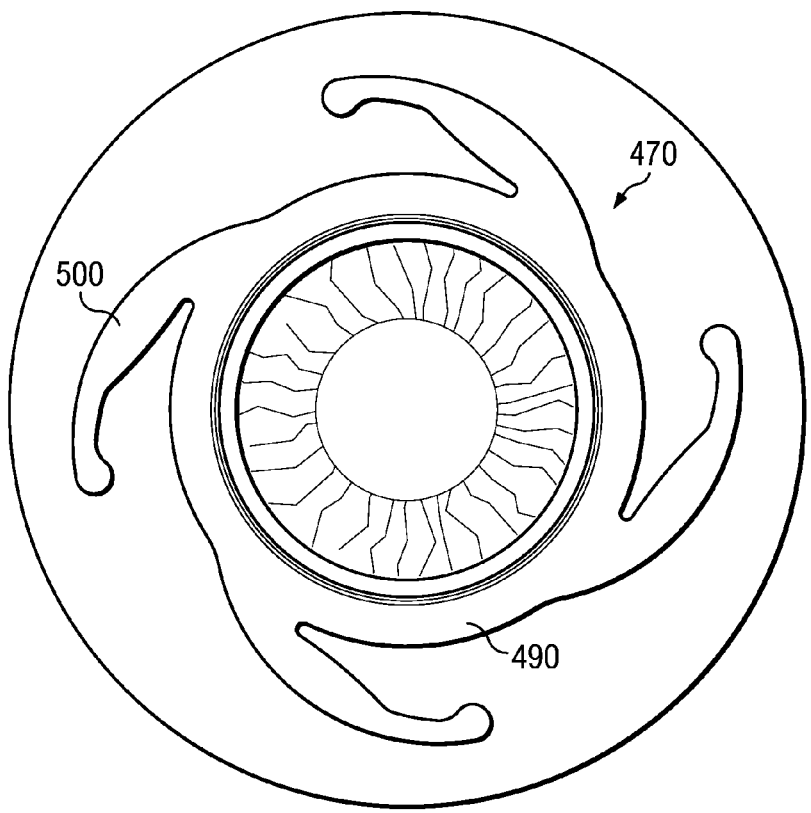
FIG. 7a illustrates a top plan view of a contact lens according to one embodiment of the present disclosure, in relation to a cornea.
Figure 7B:
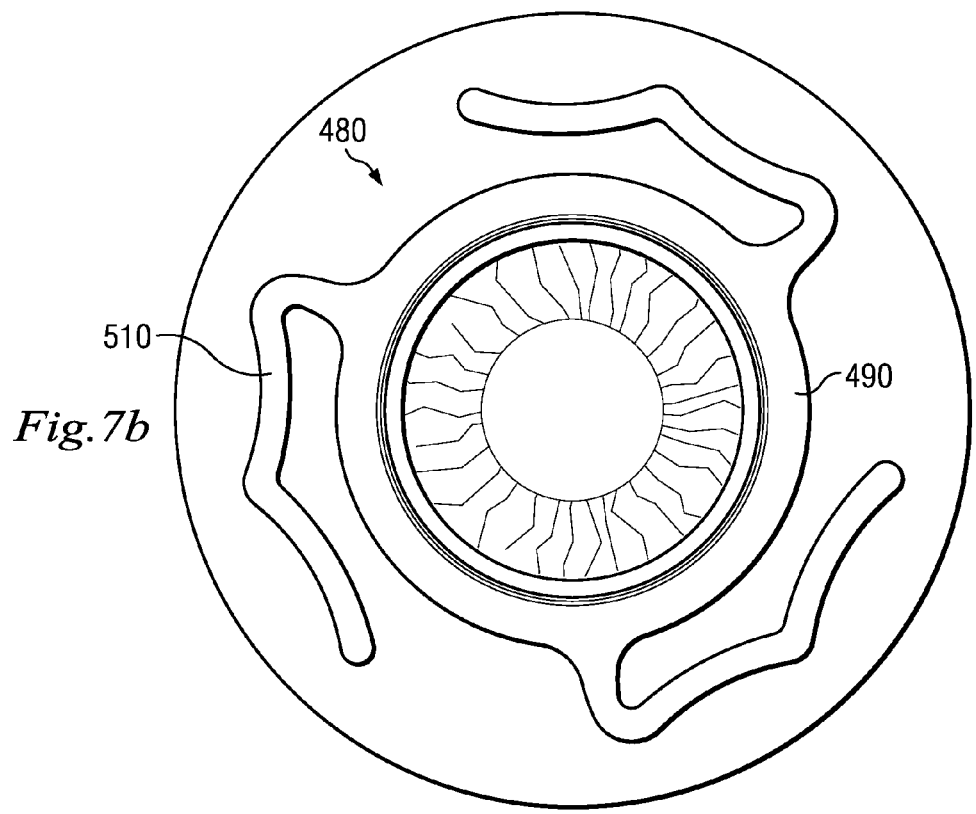
FIG. 7b illustrates a top plan view of a contact lens according to one embodiment of the present disclosure, in relation to a cornea.

FIGS. 7a and 7b illustrate surgical contact lenses 470, 480 according to two embodiments of the present disclosure. The surgical contact lenses 470, 480 are similar to the surgical contact lens 100 except for the differences noted herein. The surgical lens 470, 480 both include a flange 490. In addition, the surgical lens 470, 480 both include tabs that may extend from or swing from the flange 490 in a spiral manner. As illustrated in FIG. 7a, the lens 470 includes four tabs 500 that are slender, finger-like extensions from the flange 490. As illustrated in FIG. 7b, the lens 470 includes three tabs 510 that are relatively long, slender, finger-like extensions from the flange 490. The tabs 500, 510 may have increased elasticity and a tendency to swing from the flange 490 to contact and secure the trocar cannulas 230 during the surgical procedure. Various embodiments may include any number and arrangement of tabs 500, 510 that permit the appropriate insertion of the trocar cannulas 230 (not shown in FIGS. 7a, 7b).

Figure 8A:
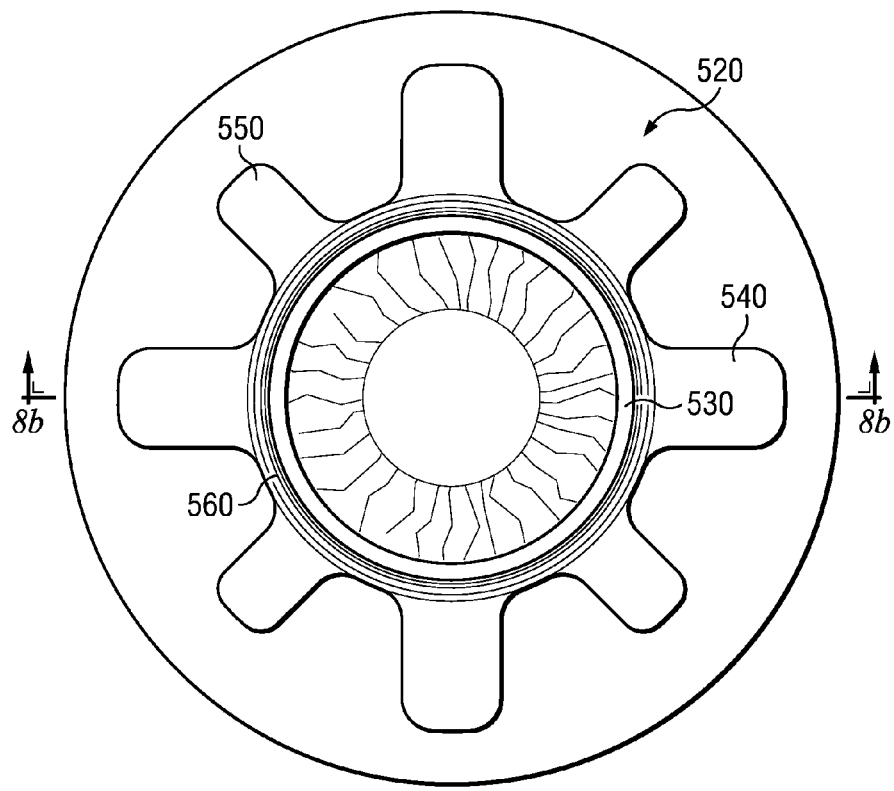
FIG. 8a illustrates a top plan view of a contact lens according to one embodiment of the present disclosure, in relation to a cornea.
Figure 8B:
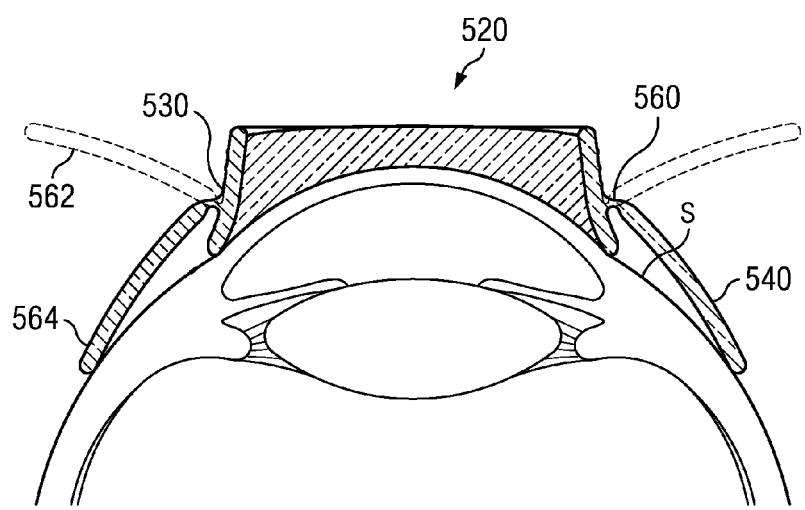
FIG. 8b illustrates a cross-sectional side view of the contact lens shown in FIG. 8a according to one embodiment of the present disclosure, positioned on an eye.

FIGS. 8a and 8b illustrate a surgical contact lens 520 according to one embodiment of the present disclosure. The surgical contact lens 520 is similar to the surgical contact lens 100 except for the differences noted herein. The lens 520 includes a rim 530 and tabs 540, 550 extending from the rim 530. In some embodiments, the tabs 540, 550 may extend directly from a flange surrounding the rim 530. The tabs 540, 550 may be shaped as finger-like or triangular extensions of different lengths. In the pictured embodiment, the tabs 540 are longer than the tabs 550, and extend further from the rim 530 than the tabs 550. Various embodiments may include any number and arrangement of tabs 540, 550 that permit the appropriate insertion of the trocar cannulas 230 (not shown in FIGS. 8a, 8b).

As shown in FIG. 8b, the tabs 540, 550 may be connected to the rim 530 by film joints 560, or areas of thinning and/or increased elasticity between the rim 530 and the integrally-extending tabs 540, 550. In other embodiments, the tabs 540, 550 may be connected to a flange by film joints 560, or areas of thinning and/or increased elasticity between a flange and the integrally-extending tabs 540, 550. The tabs 540, 550 may flip from a first, non-contacting position 562 where the tabs are not in contact with the eye to a second, contacting position 564 where the tabs contact the sclera S. Such a configuration may allow for increased adaptability of the lens to variations in eye geometry.

Figure 9A:
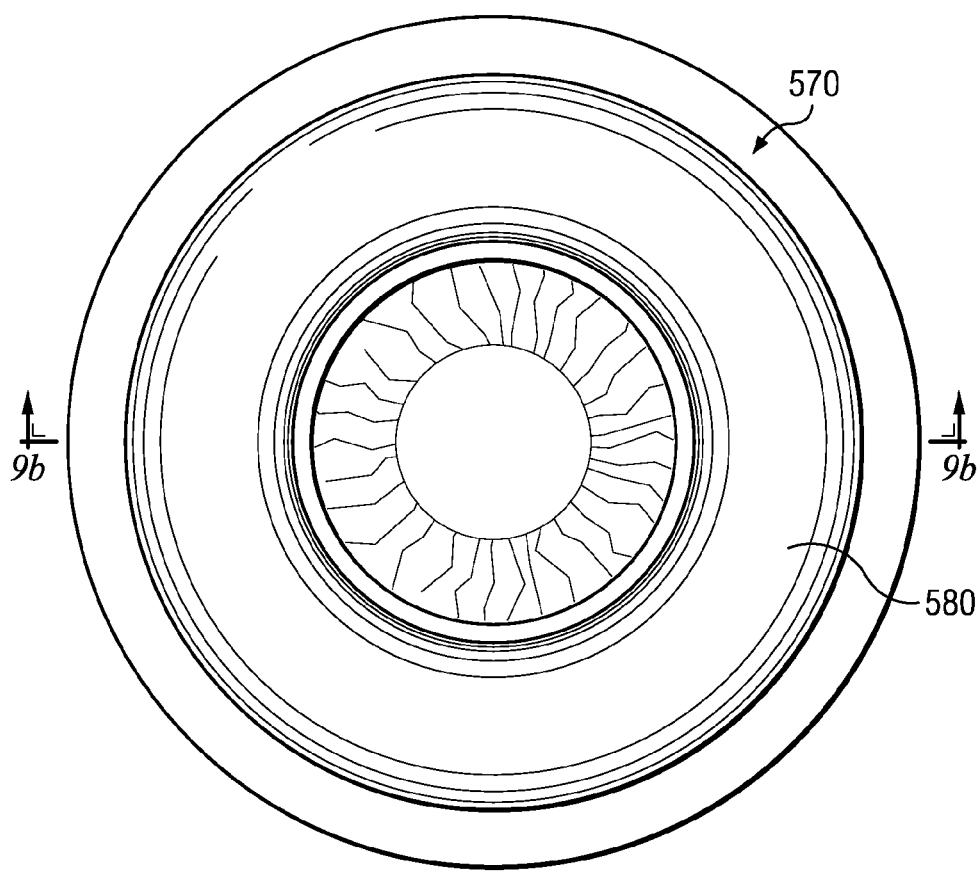
FIG. 9a illustrates a top plan view of a contact lens according to one embodiment of the present disclosure, in relation to a cornea.
Figure 9B:
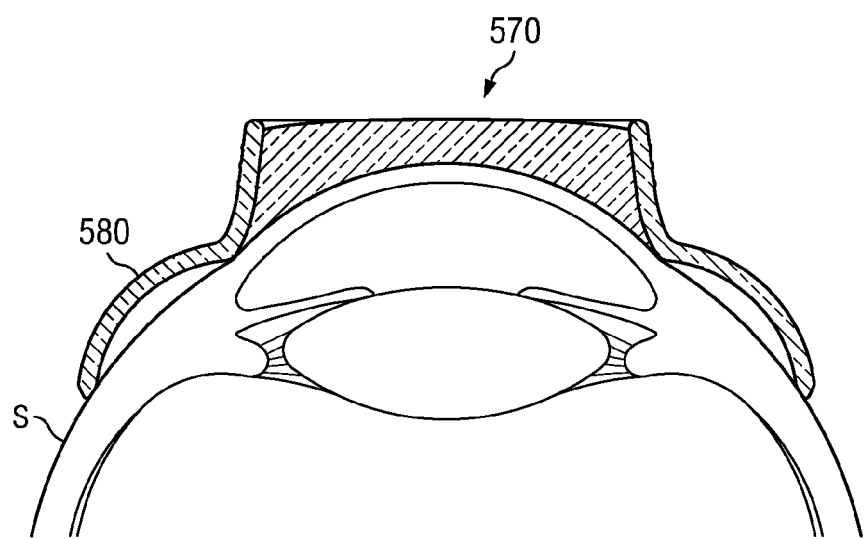
FIG. 9b illustrates a cross-sectional side view of the contact lens shown in FIG. 9a according to one embodiment of the present disclosure, positioned on an eye.

FIGS. 9a and 9b illustrate a surgical contact lens 570 according to one embodiment of the present disclosure. The surgical contact lens 570 is similar to the surgical contact lens 100 except for the differences noted herein. The lens 570 includes a flexible flange 580 that is shaped and configured as a "suction cup" that can suction the lens 570 to the sclera S of an eye.

Figure 9C:
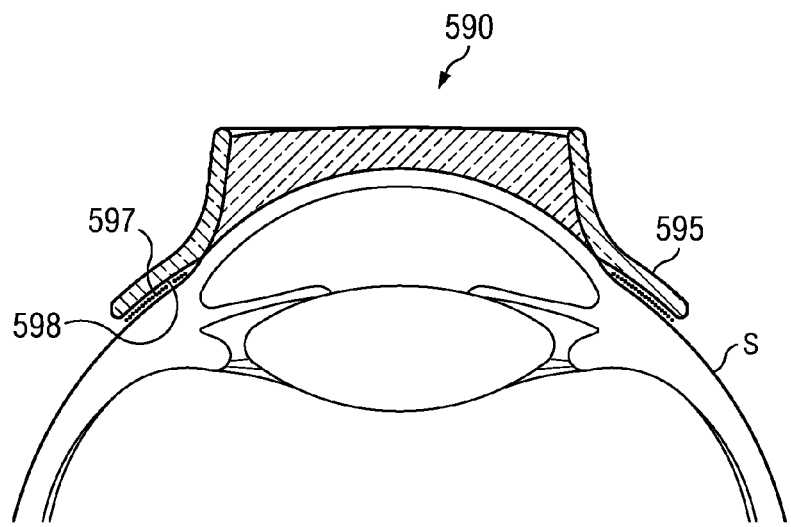
FIG. 9c illustrates a cross-sectional side view of a contact lens according to one embodiment of the present disclosure, positioned on an eye.

FIG. 9c illustrates a surgical contact lens 590 according to one embodiment of the present disclosure. The surgical contact lens 590 is similar to the surgical contact lens 570 shown in FIG. 9a except for the differences noted herein. The lens 590 includes a flexible flange 595 that may be wider than the flange 140 shown in FIG. 1. The flange 595 is shaped and configured to attach the lens 590 to the sclera S of an eye by means of an adhesive substance 597 positioned on a posterior surface 598 of the flange 595. The adhesive substance 597 may be any substance that provides temporary attachment of the lens to the eye, including, by way of non-limiting example, glue, gel, and/or tacky agent. In some embodiments, the adhesive qualities of the adhesive substance 597 may be activated by any of a variety of triggers, including, by way of non-limiting example, light, a rise in temperature, and/or humidity.

Figure 9D:
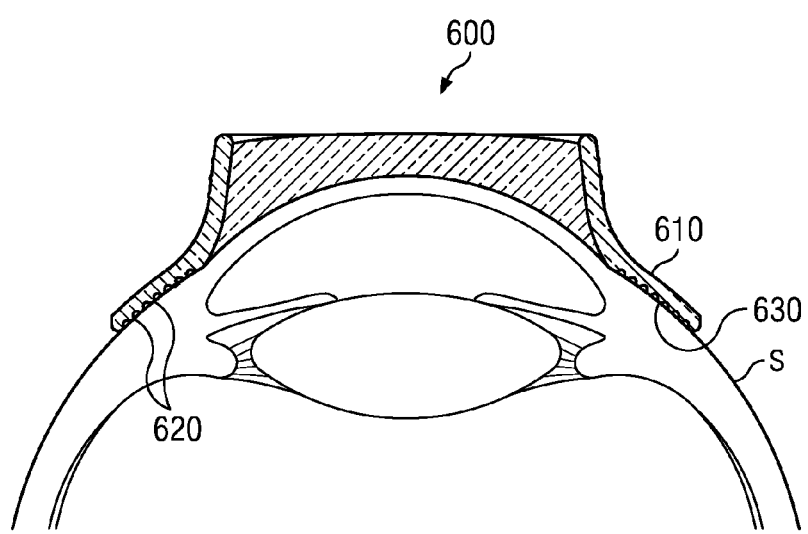
FIG. 9d illustrates a cross-sectional side view of a contact lens according to one embodiment of the present disclosure, positioned on an eye.

FIG. 9d illustrates a surgical contact lens 600 according to one embodiment of the present disclosure. The surgical contact lens 600 is similar to the surgical contact lens 570 shown in FIG. 9a except for the differences noted herein. The lens 600 includes a flexible flange 610 that may be wider than the flange 140 shown in FIG. 1. The flange 610 is shaped and configured to attach the lens 600 to the sclera S of an eye by means of a plurality of fibers 620 present on a posterior surface 630 of the flange 610. The posterior surface 630 of the flange is covered with the plurality of fibers 620, which comprise an array of soft-touch fibers that are configured to secure the lens 600 to an eye, especially when used in combination with an interface agent, such as a viscoelastic.

Figure 10A:
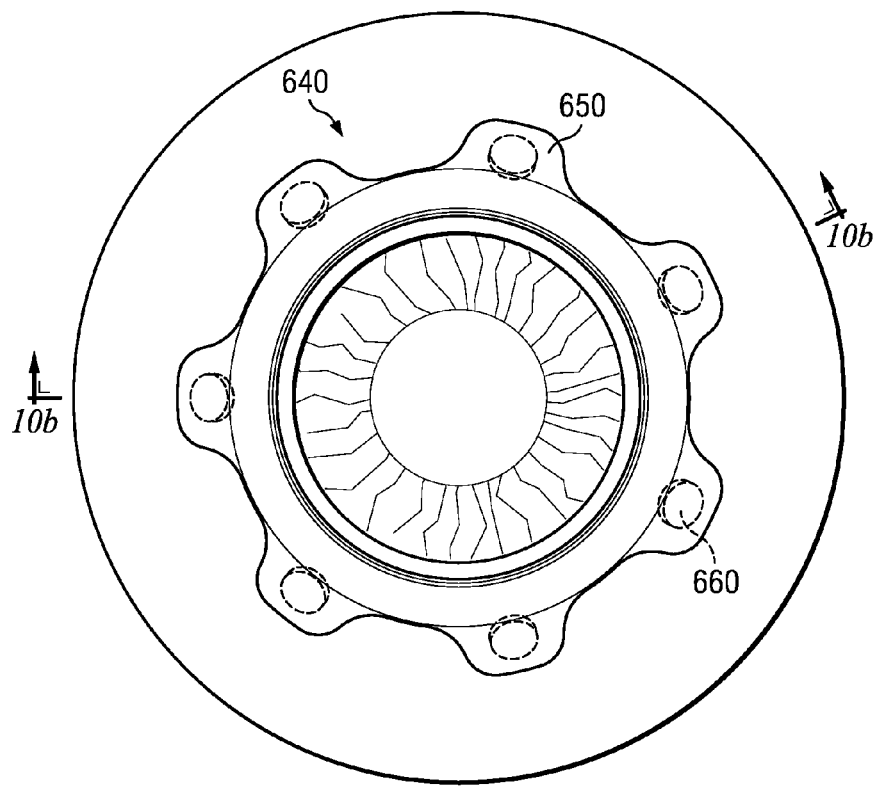
FIG. 10a illustrates a top plan view of a contact lens according to one embodiment of the present disclosure, in relation to a cornea.
Figure 10B:
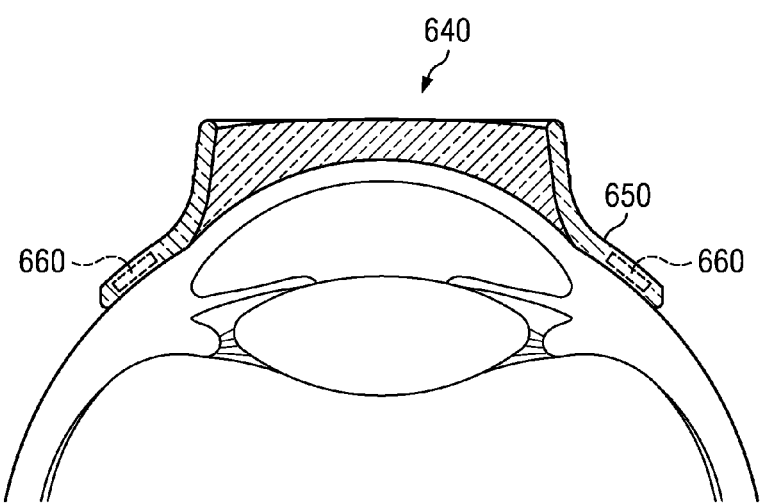
FIG. 10b illustrates a cross-sectional side view of the contact lens shown in FIG. 10a according to one embodiment of the present disclosure, positioned on an eye.

FIGS. 10a and 10b illustrate a surgical contact lens 640 according to one embodiment of the present disclosure. The surgical contact lens 640 is similar to the surgical contact lens 100 except for the differences noted herein. As shown in FIGS. 10a and 10b, the lens 640 includes seven tabs 650, each of which contain an encapsulated weight 660. Each tab 650 surrounds and encapsulates a weight 660, which is configured to secure the lens 640 to an eye by means of gravity (which increase the contact forces between the lens and the eye). Various embodiments may include any number and arrangement of tabs 650 that permit the appropriate insertion of at least three trocar cannulas 230 (not shown in FIGS. 10a, 10b).

Figure 11A:
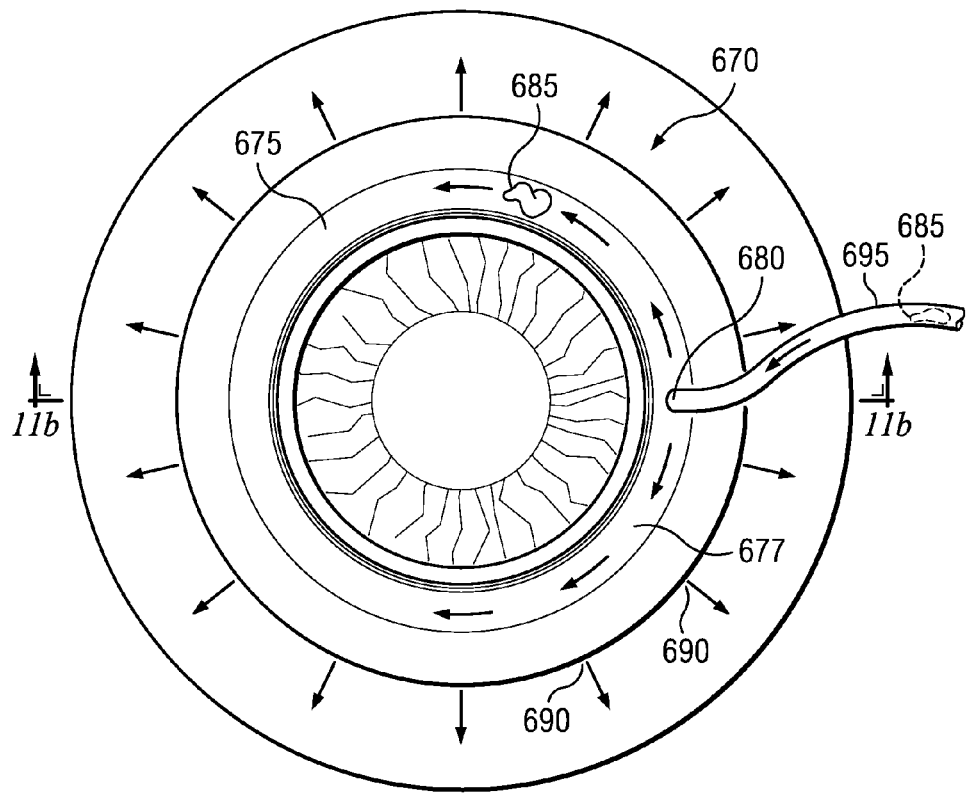
FIG. 11a illustrates a top plan view of a contact lens according to one embodiment of the present disclosure, in relation to a cornea.
Figure 11B:
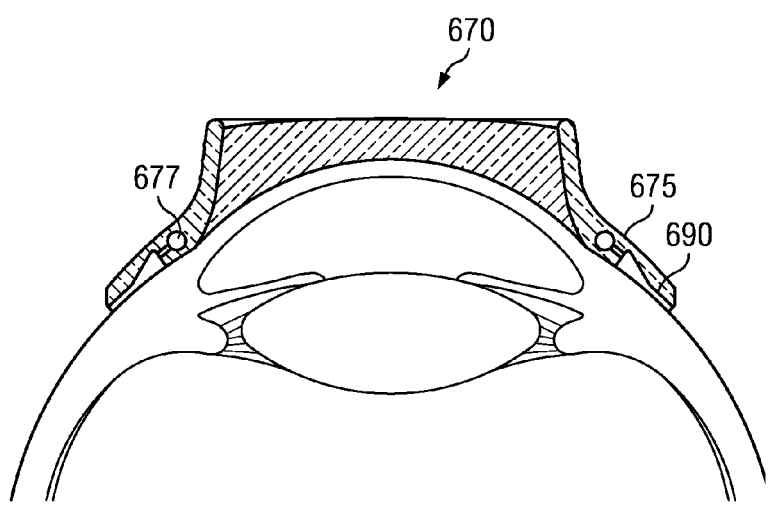
FIG. 11b illustrates a cross-sectional side view of the contact lens shown in FIG. 11a according to one embodiment of the present disclosure, positioned on an eye.

FIGS. 11a and 11b illustrate a surgical contact lens 670 according to one embodiment of the present disclosure. The surgical contact lens 670 is similar to the surgical contact lens 100 except for the differences noted herein. The lens 670 comprises a hollow flange 675 including a circumferential lumen 677 and an irrigation port 680. The flange 675 further includes a plurality of exit ports 690 that are fluidly connected to the lumen 677, which forms a generally fluid channel or tunnel extending circumferentially through the flange 675. The user may attach an irrigation line 695 (e.g., an irrigation catheter or needle) into the irrigation port 680 and continuously infuse fluid 685 into the lumen 677 throughout the ophthalmological procedure, thereby continuously humidifying the lens 670. This configuration secures the lens 670 to an eye through a Venturi effect. As the fluid 685 continuously and circumferentially exits the flange 675 through the exit ports 690, the lens 670 is vacuumed or drawn against the eye. Various embodiments may include any number and arrangement of irrigation ports and exit ports that secure the lens 670 against the eye and permit the appropriate insertion of at least three trocar cannulas 230 (not shown in FIGS. 11a, 11b).

Figure 12A:
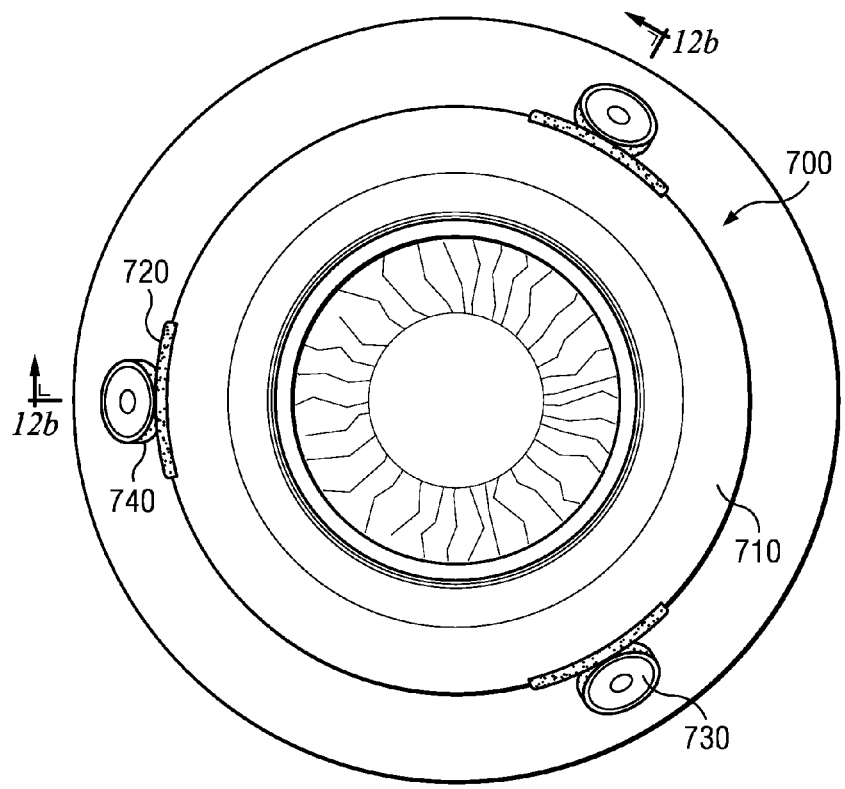
FIG. 12a illustrates a top plan view of a contact lens according to one embodiment of the present disclosure, in relation to a cornea.
Figure 12B:
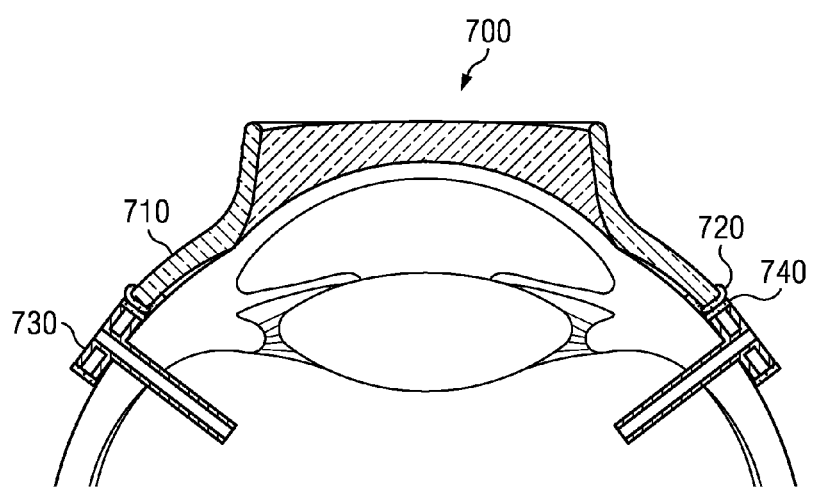
FIG. 12b illustrates a cross-sectional side view of the contact lens shown in FIG. 12a according to one embodiment of the present disclosure, positioned on an eye.

FIGS. 12a and 12b illustrate a surgical contact lens 700 according to one embodiment of the present disclosure. The surgical contact lens 700 is similar to the surgical contact lens 100 except for the differences noted herein. The lens 700, which comprises a flange 710 including attachment sites 720, is configured for temporary attachment to surgical instruments in the surgical field, including, by way of non-limiting example, trocar cannulas 730, which are similar to the trocar cannulas 230. FIG. 12a illustrates the trocars 730 secured against the attachment sites 720 of the lens 700. The trocar cannulas 730 include attachment sites 740. The attachment sites 720, 740 comprise mating halves of a temporary attachment interface, which may be configured as hook and loop closures. For example, in the pictured embodiment, the attachment sites 720 form the loop half which mates or attaches to the hook half present on the attachment sites 740. This configuration removably secures the lens 700 to the trocars 730, thereby securing the position of the lens 700 against the eye (at least while the trocars 730 are positioned on the eye). However, any other mating attachment sites or fastening means, such as, by way of non-limiting example, adhesive, glue, tacky material, and/or mechanical fasteners, may also be used to secure the lens to the trocars, and, consequently, the eye. Various embodiments may include any number and arrangement of attachment sites 720 that secure the lens 700 against the eye and permit the appropriate insertion of the trocar cannulas 730.

Figure 13:
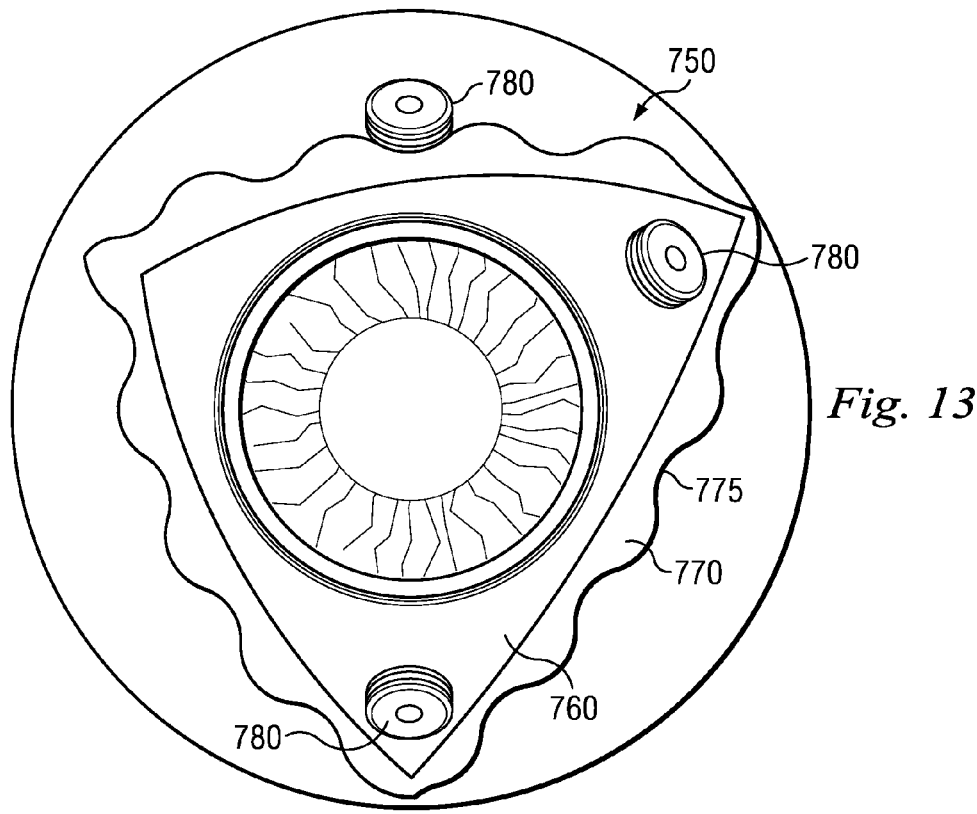
FIG. 13 illustrates a top plan view of a contact lens according to one embodiment of the present disclosure, in relation to a cornea.

FIG. 13 illustrates a surgical contact lens 750 according to one embodiment of the present disclosure. The surgical contact lens 750 is similar to the surgical contact lens 100 except for the differences noted herein. The lens 750 includes a flange 760 that is shaped and configured as a flexible, asymmetric triangle. The flange 760 includes a flexible fringe 770 that includes indentations 775 that may be shaped and sized to correspond to trocar cannulas 780, which are similar to the trocar cannulas 230. The trocar cannulas 780 may be inserted through the flange 760 or against the fringe of the lens 750.

Figure 14A:
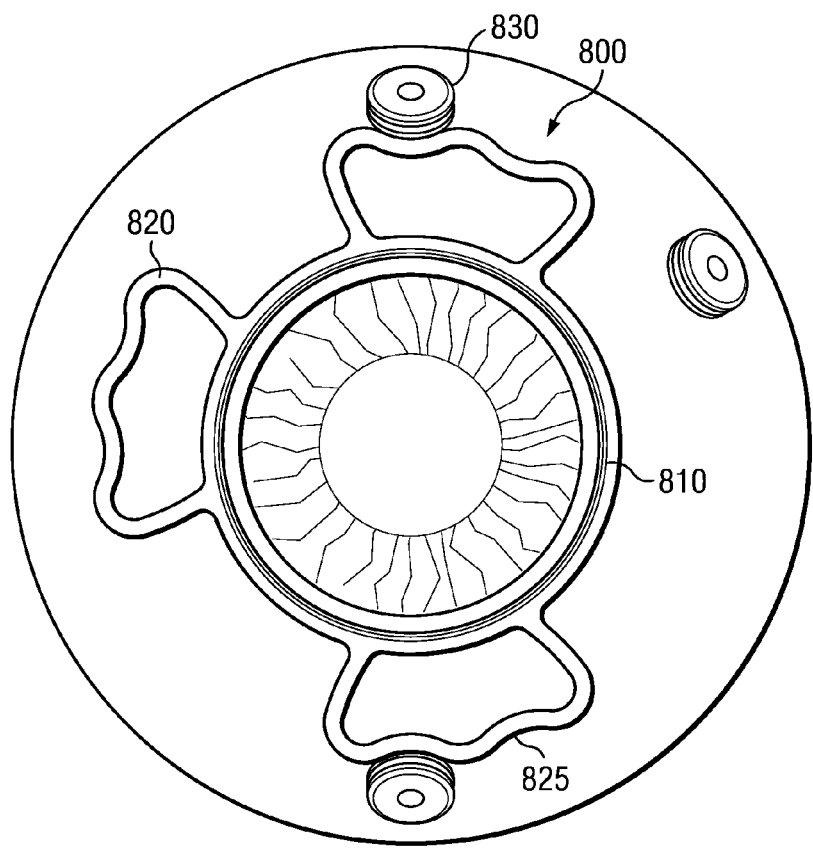
FIG. 14a illustrates a top plan view of a contact lens according to one embodiment of the present disclosure, in relation to a cornea.

FIG. 14a illustrates a surgical contact lens 800 according to one embodiment of the present disclosure. The surgical contact lens 800 is similar to the surgical contact lens 100 except for the differences noted herein. The lens 800 includes a flexible flange 810 and three tabs 820, which extend from the flange 810. The tabs 820 are shaped and configured to have curvilinear perimeters that include indentations 825, which are shaped and sized to correspond to trocar cannulas 830, which are similar to the trocar cannulas 230. The tabs 820 may secure the lens 800 against the eye by contacting and applying constant force against the trocar cannulas 830. In some embodiments, the tabs 820 may be compressed against the trocar cannulas 830 to create a clamping force that stabilizes the position of the lens 800. In other embodiments, the trocar cannulas 830 may be positioned through the tabs 820. Various embodiments may include any number and arrangement of tabs 820 and indentations 825 to secure the lens 800 against the eye by abutting and/or engaging trocar cannulas 830.

Figure 14B:
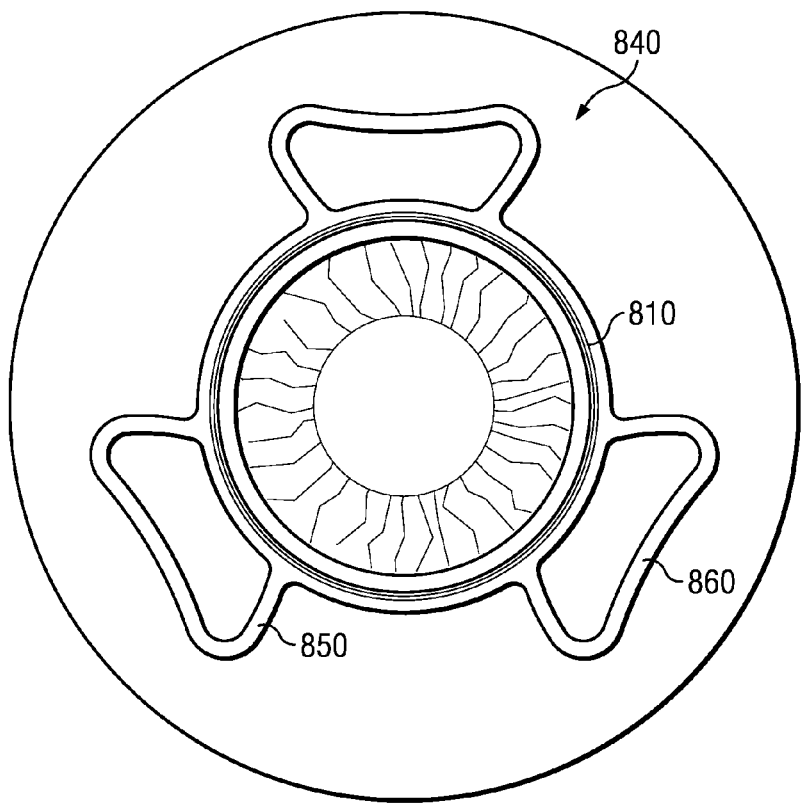
FIG. 14b illustrates a top plan view of a contact lens according to one embodiment of the present disclosure, in relation to a cornea.

FIG. 14b illustrates a surgical contact lens 840 according to one embodiment of the present disclosure. The surgical contact lens 840 is similar to the surgical contact lens 800 shown in FIG. 14a except for the differences noted herein. The lens 840 includes tabs 850 that are shaped and configured to have substantially flat perimeters 860.

Figure 15:
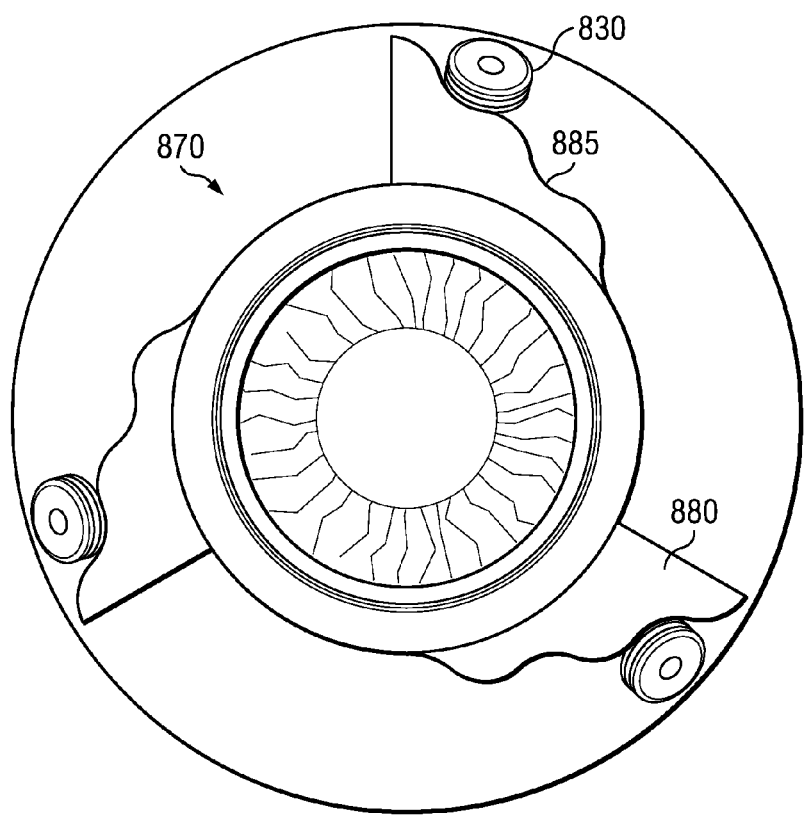
FIG. 15 illustrates a top plan view of a contact lens according to one embodiment of the present disclosure, in relation to a cornea.

FIG. 15 illustrates a surgical contact lens 870 according to one embodiment of the present disclosure. The surgical contact lens 870 is similar to the surgical contact lens 800 shown in FIG. 14a except for the differences noted herein. The lens 870 includes tabs 880 that are shaped and configured to have generally sail-shaped or fin-shaped outlines with indentations 885. The indentations 885 are shaped and sized to receive the trocar cannulas 830. By turning the lens clockwise, the tabs 880 become locked between the trocar cannulas 830. In some embodiments, the tabs 880 are shaped and configured such that counterclockwise motion of the lens serves to lock the tabs 880 between the trocar cannulas 830.

Figure 16:
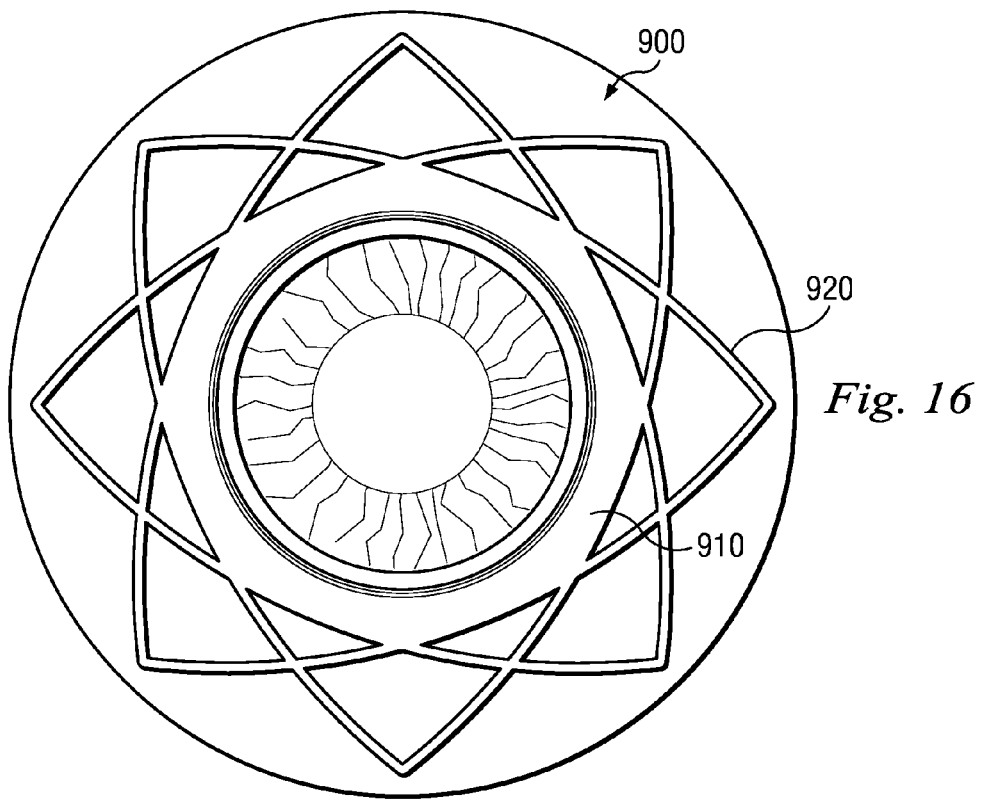
FIG. 16 illustrates a top plan view of a contact lens according to one embodiment of the present disclosure, in relation to a cornea.

FIG. 16 illustrates a surgical contact lens 900 according to one embodiment of the present disclosure. The surgical contact lens 900 is similar to the surgical contact lens 100 except for the differences noted herein. The lens 900 includes a flange 910 from which extends an interlaced grid of flexible strings 920, which serves as a viscoelastic carrier or scaffold that keeps the interface solution in place under the lens 900 to increase the shear forces between the ocular tissue and the lens. In the pictured embodiment, the strings 920 are shaped and configured to form a generally star-shaped grid. In other embodiments, the strings may be arranged into any of a variety of shapes. The strings may be formed from any of a variety of biocompatible materials, including, by way of non-limiting example, metals such as stainless steel, titanium, nickel titanium alloy, polymers such as thermoplastic elastomer (TPE), silicone rubber, polyamide (PA), polypropylene (PP), polyethylene (PE), cyclo olefin copolymer (COC), polymethylmethacrylate (PMMA), polyethylene terephthalate (PET), polycarbonate (PC), polyvinyl chloride (PVC), polyetheretherketone (PEEK), polyether block amide (PEBAX), polyoxymethylene (POM), polyglycolic acid (PGA), polylactic acid (PLA), or other types of material such as cotton or glass fibers, all of which may be in a monofilament or a multifilament configuration.

Figure 17:
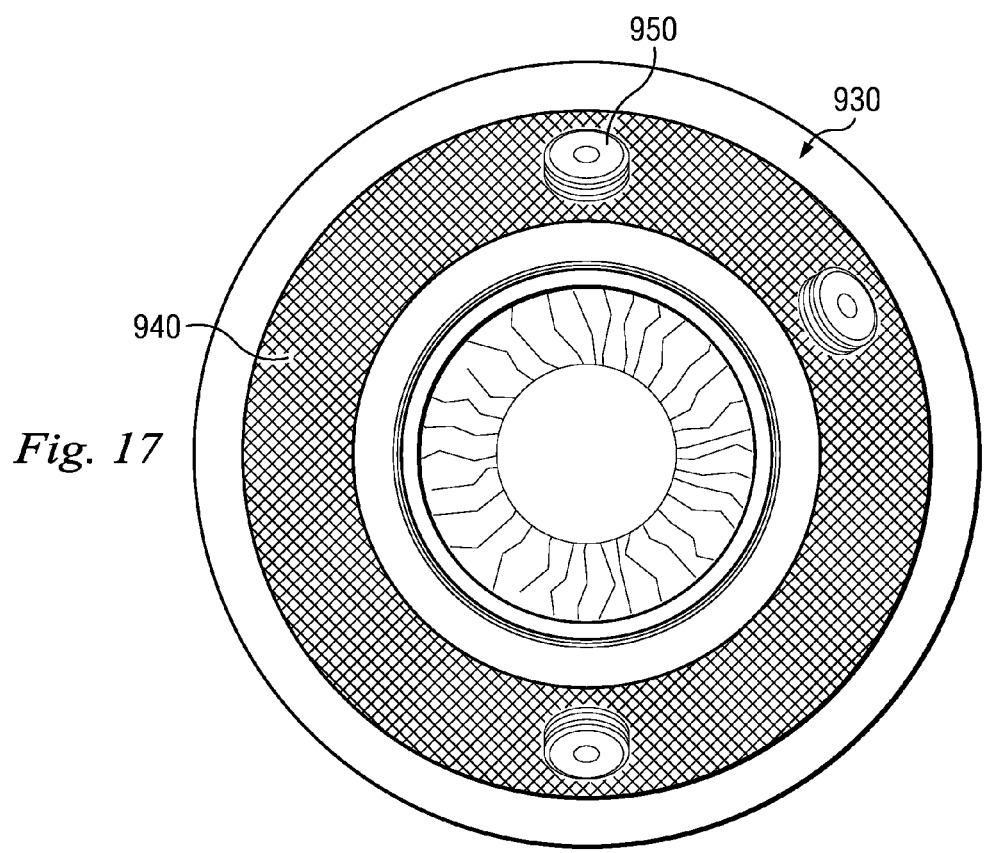
FIG. 17 illustrates a top plan view of a contact lens according to one embodiment of the present disclosure, in relation to a cornea.

FIG. 17 illustrates a surgical contact lens 930 according to one embodiment of the present disclosure. The surgical contact lens 930 is similar to the surgical contact lens 100 except for the differences noted herein. The lens 930 includes a flange 940 that is comprised of a mesh structure, which serves as a viscoelastic carrier or scaffold that keeps the interface solution in place under the lens 900 to increase the shear forces between the ocular tissue and the lens. The mesh structure may be composed of any of a variety of biocompatible materials, including, by way of non-limiting example, surgical mesh, textiles, gauze and/or sponge, each of which may be made of either a natural material (cotton and derivatives) or polymers such as, by way of non-limiting example, silicone rubber, TPE, PA, PP, PE, COC, PMMA, PET, PC, PVC, PEEK, PGA, PEBAX, POM, PGA, and PLA. Trocar cannulas 950, which are similar to the trocar cannulas 230, may be inserted through the flange 940 to secure the lens 930 against an eye.

The surgical contact lens embodiments described herein may formed from any of a variety of biocompatible materials, including, by way of non-limiting example, PMMA, Zeonex, Topas, silicon rubber, Acrysof, PC, acrylic, epoxy, polysulfone (PS), polyphenylsulfone (PPSU), Polyetherimide (PEI), and/or PET. In some embodiments, the various components of the contact lens, including the optic, the flange, the rim, and the tabs, are formed from the same biocompatible material. In other embodiments, the various components of the contact lens are formed from different biocompatible materials. Desirable materials for forming the contact lens include cyclo olefin copolymers, which are like polyethylene, but have a cyclic structure. These modern materials, which are state of the art for optical devices, possess good color transmittance and reduced chromatic aberration in comparison to traditional lens materials while simultaneously allowing for a thinner optic due to a high refractive index and allowing for application of an antireflective coating. Thus, the surgical contact lenses of the present disclosure provide an optic well-suited for visualization of and operation within the posterior segment as a result of their high optical quality, high level of detail discrimination, smaller field of view if necessary, and by providing a non-inverted (upright) image.

The various surgical contact lens embodiments of the present disclosure may be configured as single-use contact lens that are intended to be disposable after a single use, thereby allowing for optimum optics for each new patient. As such, the contact lens may be pre-sterilized before shipping to an end-user and ready for use upon receipt by the end-user. After a single use, the contact lens may be discarded. Single-use contact lenses ensure a sterile lens for each patient without the need for sterilization by the end-user (i.e., the surgeon), thereby increasing the efficiency and safety of the ophthalmological procedure. Moreover, configuration as a single-use contact lens allows the surgical contact lens to be manufactured at lower cost because the disposable lens can be constructed of a relatively inexpensive biocompatible material, such as, by way of non-limiting example, a plastic, rather than optical glass. For example, some embodiments of the lens provide disposable complements to several contact lens systems, both direct and indirect, and/or any non-contact viewing system for macular work.

Figure 18A:
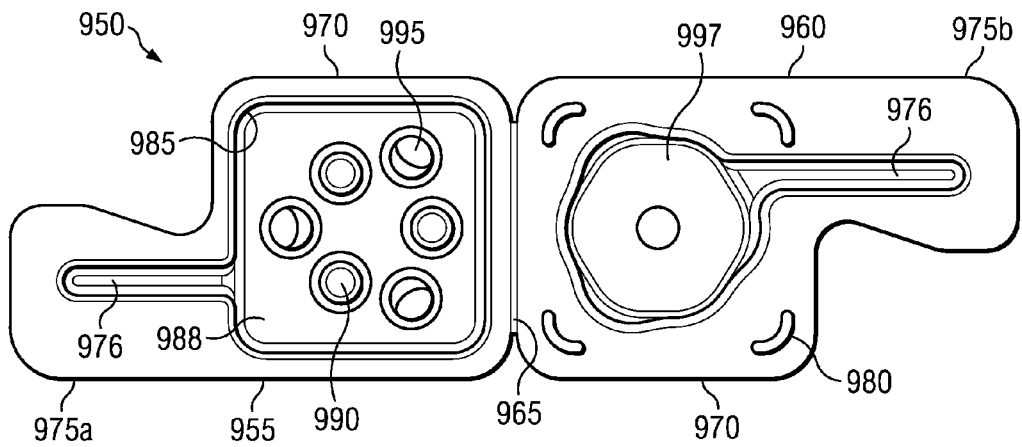
FIG. 18a illustrates a top plan view of a packaging case in an open condition according to one embodiment of the present disclosure.
Figure 18B:
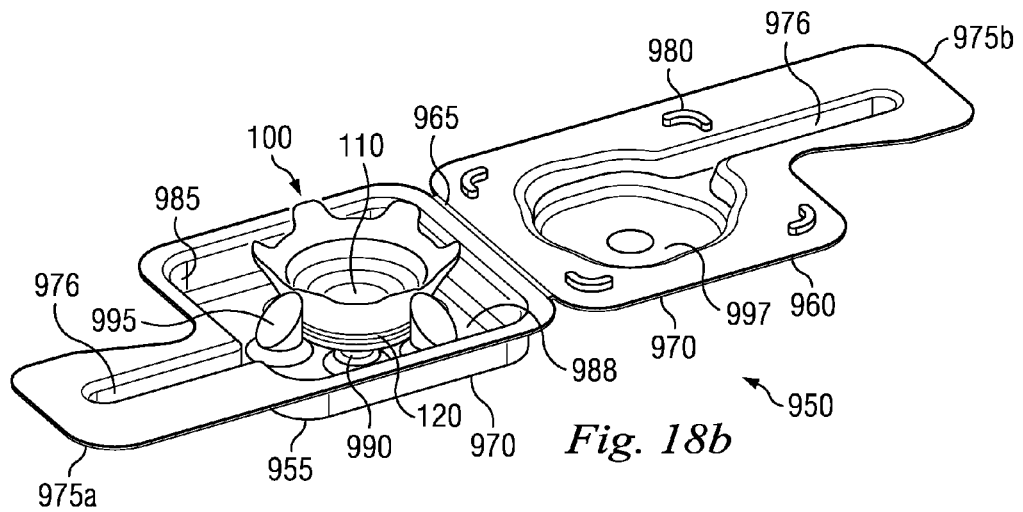
FIG. 18b illustrates a perspective view of a packaging case shown in FIG. 18a in an open condition according to one embodiment of the present disclosure (and containing the surgical contact lens shown in FIG. 1).
Figure 18C:
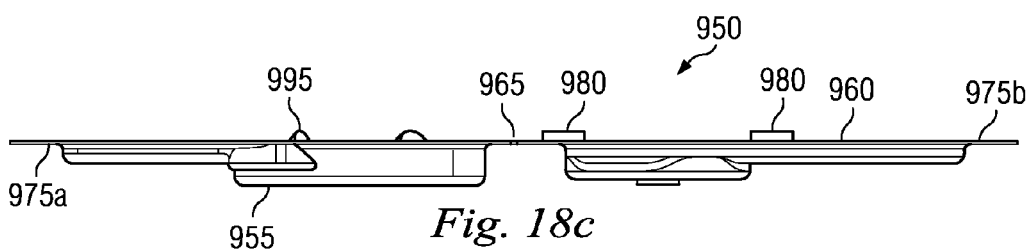
FIG. 18c illustrates a side view of the packaging case shown in FIG. 18a in an open condition according to one embodiment of the present disclosure.

FIGS. 18a-18d illustrate an exemplary packaging case 950 to protect and contain the various surgical contact lens embodiments of the present disclosure. As shown in the top view presented by FIG. 18a, the packaging case 950 comprises a clamshell packaging container including a bottom half or portion 955 and a top half or portion 960 that are connected to each other by a foldable connecting portion 965. As shown in FIGS. 18a and 18b, the bottom and top halves 955, 960 are shaped as generally rectangular containers 970 having tails 975a and 975b, respectively. The tail 975a is an integral part of the bottom half 955, and the tail 975b is an integral part top half 960. Each of the tails 975a, 975b include a channel 976 extending from each container 970, which allows sterilization media (e.g., by way of non-limiting example, ethelene oxide) to enter the case 950. The foldable connecting portion 965 is shaped and configured to flexibly connect an edge of the bottom half 955 to an edge of the top half 960. The bottom half 955 and the top half 960 are shaped and configured to allow the top half 960 to fold into and partially nest inside the bottom half 955, thereby closing the case 950 and securely containing the lens therein. The configuration of the case 950 allows the lens to be carried within a sterile environment and permits an easy sterile field transfer of the lens in the operating room.

Figure 18D:
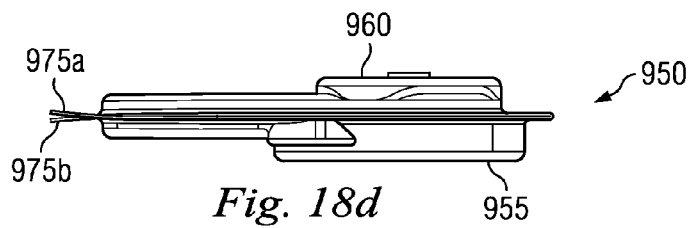
FIG. 18d illustrates a side view of the packaging case shown in FIG. 18a in a closed condition according to one embodiment of the present disclosure.

As shown in FIG. 18d, the top half 960 may be closed against the bottom half 955 to contain the lens within in a secure manner. The case 950 is shaped and configured so as to secure a lens of the present disclosure (e.g., the lens 100) in a generally snug and form-fitting manner. The case 950 includes protrusions and cavities so as to cushion and protect the lens 100 within the case 950. The top half or portion 960 and the bottom half or portion 955 of the case 950 may be secured together using any appropriate means. For example, in the pictured embodiment, a snap fit engagement using friction fit engagements between portions of the top half 960 and the bottom half 955 are used to secure the top half 960 against the bottom half 955 in a closed position. In particular, the top half 960 includes protrusions 980 that are shaped and configured to engage with and "friction fit" to internal corner wall recesses 985 of the bottom half 955. In addition, the tails 975a, 975b are shaped and configured to interlock, as best shown in FIG. 18d, thereby securing the top half 960 against the bottom half 955 in a closed position.

As shown in FIG. 18b, the lens 100 may be seated flat within a generally square-shaped well 988 of the bottom half 955. The optic 110 and/or the rim 120 may be positioned on shallow projections 990 and between high projections 995. The top half 960 includes an irregularly-shaped well 997 that is shaped and configured to accommodate the tabs 150 of the lens 100. In other embodiments, the wells 988, 997 may be shaped and configured to accommodate various embodiments of surgical contact lens disclosed herein in a form-fitting, secure, and protected manner. In some embodiments, the case 950 may be shaped and configured to have multiple wells to contain more than one surgical contact lens at one time.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

I claim:

1. An ophthalmoscopic contact lens comprising:
   an optic including an anterior surface having an aspheric base profile and a posterior surface having a shape substantially corresponding to a shape of a cornea of an eye;
   a flange integrally formed with the optic and surrounding the optic, wherein the flange has a curvature substantially corresponding to the curvature of a sclera of an eye; and
   an integrally formed rim comprising a cylindrical tube that circumferentially surrounds the optic and extends above the anterior surface of the optic, opposite the flange, to form a protective ridge around a peripheral circumference of the anterior surface of the optic.

2. The ophthalmoscopic contact lens of claim 1, wherein the rim includes a gripping feature.

3. The ophthalmoscopic contact lens of claim 1, further including a plurality of tabs extending from the flange, each having a curvature substantially corresponding to the curvature of a sclera of an eye.

4. The ophthalmoscopic contact lens of claim 3, wherein the plurality of tabs are equally sized.

5. The ophthalmoscopic contact lens of claim 3, wherein the plurality of tabs include tabs of varying sizes.

6. The ophthalmoscopic contact lens of claim 3, wherein the plurality of tabs are equally spaced around the flange.

7. The ophthalmoscopic contact lens of claim 3, wherein individual tabs of the plurality of tabs each encapsulate a weight.

8. The ophthalmoscopic contact lens of claim 3, wherein the plurality of tabs include tabs each having a flexible perimeter shaped and sized to engage a trocar cannula.

9. The ophthalmoscopic contact lens of claim 1, wherein the flange includes at least one attachment site configured to mate with a trocar cannula having at least one complementary attachment site.

10. The ophthalmoscopic contact lens of claim 1, wherein a plurality of tabs integrally extend from the rim and are shaped and configured to flip toward and away from a sclera of the eye at a film joint between the rim and the plurality of tabs.

11. An ophthalmoscopic contact lens comprising:
    an optic including an anterior surface having an aspheric base profile and a posterior surface having a shape substantially corresponding to a shape of a cornea of an eye;
    a flange integrally formed with the optic and surrounding the optic, wherein the flange has a curvature substantially corresponding to the curvature of a sclera of the eye; and
    a plurality of tabs extending from the flange and having a curvature adapted to fit a sclera of the eye;
    an integrally formed rim comprising a cylindrical tube that circumferentially surrounds the optic and includes gripping features encircling an outer surface of the rim that are configured to allow a user to manipulate the contact lens when the contact lens is lying on an outer surface of an eye.

12. The ophthalmoscopic contact lens of claim 11, wherein the plurality of tabs include adhesive to adhere the lens to the eye.

13. The ophthalmoscopic contact lens of claim 11, wherein the plurality of tabs include a plurality of fibers to secure the lens to the eye.

14. The ophthalmoscopic contact lens of claim 11, wherein the anterior surface of the optic includes an anti-reflective coating.

15. The ophthalmoscopic contact lens of claim 11, wherein the flange includes at least one attachment site configured to mate with a trocar cannula having at least one complementary attachment site.

16. An ophthalmological surgical system, comprising:
    a surgical contact lens, the lens comprising:
      an optic including an anterior surface having an aspheric base profile and a posterior surface having a shape substantially corresponding to a shape of a cornea of an eye; and
      a flange integrally formed with the optic and surrounding the optic; and
    a packaging case comprising a top portion and a bottom portion, wherein the top portion and the bottom portion are shaped and configured to close together and contain the lens.

17. The system of claim 16, wherein the top portion includes one of a protrusion and a recess and the bottom portion includes the other of the protrusion and the recess such that the top portion and the bottom portion define a cavity substantially surrounding the lens when the recess receives the protrusion.

18. The system of claim 16, wherein the top portion includes a first tail portion and the bottom portion includes a second tail portion, wherein the tail portions interlock to secure the top portion against the bottom portion.

19. The system of claim 16, wherein the lens further comprises a rim extending from an anterior surface of the flange to and beyond the anterior surface of the optic, and wherein the bottom portion includes a first set of projections upon which the rim of the lens securely rests.

20. The system of claim 19, wherein the lens further comprises at least one tab extending from the flange and wherein the bottom portion further comprises a second set of projections, such that the at least one tab is secured in place within the bottom portion by the second set of projections when the rim of the lens securely rests on the first set of projections.

\* \* \* \* \*